US008648230B2

(12) United States Patent
Held et al.

(10) Patent No.: US 8,648,230 B2
(45) Date of Patent: Feb. 11, 2014

(54) REGULATORY REGIONS PREFERENTIALLY EXPRESSING IN NON-POLLEN PLANT TISSUE

(75) Inventors: Bruce Held, Ames, IA (US); Vaithilingam Sekar, Ames, IA (US); Janell C. Eby, Ames, IA (US); Carol J. Lewnau, Ames, IA (US); Penny Perkins, Granger, IA (US)

(73) Assignee: MS Technologies, LLC, West Point, IA (US)

( * ) Notice: Subject to any disclaimer, the term of this patent is extended or adjusted under 35 U.S.C. 154(b) by 317 days.

(21) Appl. No.: 13/051,358

(22) Filed: Mar. 18, 2011

(65) Prior Publication Data
US 2012/0240291 A1 Sep. 20, 2012

(51) Int. Cl.
C12N 15/82 (2006.01)
C12N 5/04 (2006.01)
C07H 21/04 (2006.01)

(52) U.S. Cl.
USPC ........... 800/278; 800/287; 800/288; 435/419; 435/468; 536/24.1; 536/23.1

(58) Field of Classification Search
None
See application file for complete search history.

(56) References Cited

U.S. PATENT DOCUMENTS

| 6,222,096 B1 | 4/2001 | Held |
| 7,223,569 B2 | 5/2007 | Held |
| 7,393,948 B1 * | 7/2008 | Sekar et al. ........... 536/24.1 |
| 2006/0048240 A1 * | 3/2006 | Alexandrov et al. ......... 800/278 |
| 2009/0320160 A1 | 12/2009 | Li |

FOREIGN PATENT DOCUMENTS

| WO | WO0040710 A2 | 7/2000 |
| WO | WO03104465 A1 | 12/2003 |
| WO | WO2006053169 A1 | 5/2006 |
| WO | WO2006102343 A2 | 9/2006 |

OTHER PUBLICATIONS af055369_1998.*
AF108084_2003.*
Moran et al., Plant Phys 133:773_2003.*
Komarnytsky Genetic Engin_25_113_2003.*
Donald_EMBO J_9_1717_1990.*
Kim_Plant Mol Biol_24_105_1994.*
Dolferus_Plant Phys_105_1075_1994.*
PCT International Search report for PCT/US2012/028040, Aug. 27, 2012.
EMBL XP-002675841, GenBank AF055369.2 "Glycine max nitrate reductase (nr2) gene, partial cds" Apr. 6, 1998.
www.phytozome.net/search.php?show=blast&blastdb=soybean, University of California Regents, Center for Integrative Genetics, 2010.

(Continued)

Primary Examiner — Shubo (Joe) Zhou
Assistant Examiner — Russell Boggs
(74) Attorney, Agent, or Firm — Patricia A. Sweeney

(57) ABSTRACT

Regulatory regions are shown which regulate expression of an operably linked heterologous nucleic acid molecule in plants. Promoters are described which express at lower levels in pollen cells that in other plant cells. Methods of using such promoter to regulate expression of an operably linked nucleic acid molecule are described. A polyadenylation nucleotide sequence from soybean is further shown.

12 Claims, 11 Drawing Sheets

(56) References Cited

OTHER PUBLICATIONS

Cho et al. "Regulation of root hair initiation and expansins gene expression in *Arabidopsis*" Plant Cell., vol. 14, 3237-3253 (2002).

Moran et al."Functional characterization and expression of a cytosolic iron-superoxide dismutase from cowpea root nodules" Plant Physiology, vol. 133 pp. 773-782 (2003).

* cited by examiner

Figure 1

Nucleotide sequence of GNR promoter (1059 bp)

```
GATCTTCATTTATCCATGGGGTACTTGTTCTTTATGTTTTATATATTTCTGTCACTCTCTCTAATTTCTTTACA
CGAATACTTTTTACTTTTATTGAAAAACATAGGATATGTATGAATACATCACTGCACTTTACTTTCATGCATGGA
TATTGTTCAATTTCTTAATAGAATTTATCACAGACCCACACCCAAACTTGCTTAGTAACCTAAACTAATTTAATAA
AATAAAAAAAATCCCTATTACATTGATTTTTGTTTGAGGAATAACTATTTTTTCTTTTACATTGATTTTATTTTA
TTAGTATTAGTTAAACTTGGATTCAATTTTTCAGTTAAAAAAACTGGGATCAATTTCAATCTTAAATTAAATATC
CTTAATATTAAAGAGTCTAACTCAATTAATTTAATAATGTGTAAGATATTATAAGTTTTTTGATTAAGTTCAATTCA
TACAATAAAATAAAATAGATAATGACAAGAGATGTTGAAATATGTAAATCTAACCTAATTTAATGCAACTCGTCATT
CATAAAAAAAGCGATTGCATTGTGTTAGAAATTCAATGTAACCAATCCTGATATAAATTGTGCGTACGATAGG
ATGCAAACTTACAATGCAACTATTTCTTTTATTTGTTAAAAATGATATTTTTATTTTTAAAATATAAAATTTATA
AATATAATAAATAATACATAATAAGTTATAAAATTTAAAAATGATATTTTTATTTTTAAGAAACAAAATCGCTAA
ATTAGTTGAGAATGCAAAACTTTTAAAATACTACTCCATTTACTATAATTTTGAAATAAATTGGTCTGACATAG
CCATAGTACACAGTCTTTTCTCGATACTGGGTTGGTTACGTCTCTTCCCCACGACGGCTCGGAAGCTCGCCC
AATCCCTCCATCTTCACTCGTTCAAAAACAAAACCATTCTACCTCTCCAAAACCATCGAACTCTCATGTTCGAAG
AAAACATACACAATGCTTCAAACTGTAATTTCTTTTCTTTCATTTAATTTCCTCA
```

Figure 2

Nucleotide sequence of GSO promoter (884 bp):

GAAGAAGATCTAGTTCACTGGTTAAATAAGATGTGGGGGTATTTTTTTTTTTATCAAATGGGTGTGTGAGTGTTGT
AAATTCATAATATGTTTAATTGATACGGATAAAAATAAACCATTATAATAAAAAATTATTATTTTATATTTTAATTT
TATTTATAAACTAGCCACTAATTTTTATTAATGAAATGGTATGCATTTTTCATTATTTTTAGTTTATTTCCATAAA
TAAAATAATTTGTAGTATTTTTAAATATTTTTCAATTTTTACATATTTATTGTTATAAAATTATAATAAAATGCAT
ATGCAGAGAAAGACTTTATATTATCATTCAATCACAAATTATCATTAATTATTTTAAGATAATAATTTTAAAGATTA
TCAAAATTATCATTATGATCAATGATCTTTAAAAAAAGTTACTCTATAACTTTTTTCTCAATAAATTAACTGAAAT
AAAAATATAAAAACACACGGTATGGTCCACAAAAATTAGTTAAGAAATTAGTTTTGAAGTTCTATTTTGTTATAATT
TTTAAATCTGATGCGGTAGTAAAATTCCACAAAAATAAGTTAATAAGCACATTTAAGAAATTAAGCATTCATCCGA
GATACTCTAATTGATAATTTAAACTTTTGTGTGAGCCGTACAATTAATATAG_____GTAATAATATATA
GATACTAATCGATAAAGATGTAATAATAACGTAGAATTTGTACTGATGGGGCTGTGCTGGTCGTACCTGCACAACTT
AGTGTACTACAACATTGGAATTGTACTAACACACTTTCTTGTTTATATTGCCCTGTAAGGAATGGTAGACCTTTGT
CCAAAATCCTCACTCCAGCCACAGGCGTCAGTAGACC

Figure 3

Nucleotide sequence of promoter 17

ATCGGATCCACCCGCCCATACATCGTAACCACTATACACCATTCAAGCAATACATGCATTACATTTACACCCAATGG
TAATTACCCTGTGACCTCGCCCTACTAATTAATACTACACTCCATTCAACATTTTGCCACTGAGCATTACAAGATA
TAGCATTTTCAAGACAATGTGCAATATTAATGCATACTACTCTCCCCGAGTACACTCCAAGTCGGTGAGGAAGTATG
AACTCCAATCCGTGTTCTGGAGATGAATTTGAGTAGGTGCTGGGGTTCTGCGATACATCGTGAAAAATTCAGTTAAT
CGCCGTCTTGTCAGGAAATGCATGGCAAACATTCATCTGCCAATACAAAGAAACCCTAGTAAGACCTCATAAGCTAC
AGTACAGTAAACAGTATATGACAGACAGGATGTTGATTACATATGCGTCTCGTTTTCAAGGGACACTCCAACTCTGC
GCAAGTAGTAATCACGCACAGAGAGAGAGAGAGCAAGCAAACAGAAAAAAAATAAAAGAAAATGAAAGGAGACTTCT
TCTCATGATTGCTACGTGACGTTAGTAGTGGGAATAGAGAAAAGGAATCGAGAGAATTCTACTTTTTTATTTTTAA
GAAATAAGCATAAAATAATTCAATAACTATAATATCTTAAAACAAAAGAGACAAATGGATTTTTTTTGTCTAGAAA
AAAAGAGACTTAGCTTTACACATTATATTAATATTATATGATAACATTATCATATCTTATTAGCATAATAAATAACA
AATTACAAAATAATAGAGTAGTTATCCTTTCTTCTCCTAGTTACTTTAGGAGACCTTGTTAATTAGCTATGTAGTGA
AAGTATAACAGAGTTCAATTATCATTTAATCACTCCCTCAGAAAAAATTGATCATTTAACCACAGATATTCTTAATC
TAGCTTTTCATGCAACCCTATCCGTCTATATTACATCTCATACAATACAACCCTGCCCGTCTATATAAGGTCCACGT
ACCTTGAACGTTTTCTGCATTCTCACTATTCTCCTCATCTTCCTCTTTTTCTCAACCAAAAGGGGTTCAATTCTAGC
TAGTTCTATTACATCGTCCGCGACCATGGGAT

Figure 4

Nucleotide sequence of promoter 185

ACTGCGGCCGCGAGTATGACCCTTGATGCCGCCAAGAAAAATTTGTTCTGAATTTTCTTTTTTAAAAAGTTACCTA
TGTATTTTTTATGGGAGACTTTTTGCTCAAAGAATTATTATAAACATTAAAATATAAGTATTGACAATTATATATTT
AATAAATAAATTTAAGATTATTGATTAAACTAACATAATTTCATACTAATTAATTCATACGTTCGGTGATGTGATAG
AAATTAATATATATATATATATATATATATAGAGGTATATTTTAGTTAAATTTCTCAATAAGTTTATAAGAAAAGAA
AAGATAACCAATGTTTCTTTCATACATTAAAATCTAAATTATACACGTCAACATTTTAAAAGTTTTTTATTAAATT
ATTTTCAAAGTGATGTATAAATGTTTTGATTTTTGGAGAAAAAATTTACCTTTTCAATTTTTTTCTTATAATTACTT
ATTACTGGACACAATTTTCTTTTATCCCTTTCTAAATGTCTTTTAGGCTGAAATCAGCAATCTGGCTTTTAGACTGA
AAATAATTTCCCCGCATGTTTTGGAGTCGTCTTCCTTTTCTATCTTTTTACTCCCATTTGCTTAGAGATTGAAATTT
TGCACTACAGTGAACAGTAGGAAATAATTGCATTTCGGGTGACTTTGGCTTCAGCTTCAGCAATTCAGTGATTTCAG
TCTAATCTGTCTGTTACAATCGGTTTGACCACGAAGTTCCACCGAAAGGTACTAAAATAATGTAGATTTTCATTAAC
ATATCTAAAATTTCAACTCTGAGCTATGTGACCAAGCCATATAAAATACAAACTAGTCATATGATCTTGACCTTCGT
CCTTAGGAAGAAAAAGAAATTATAAAGTCAATATATAGATAATTACATCGATCTAAAAGTATTCAGCTATGTTAAAT
TTCTAAAATGATAAGTTTTATTAGAAAAAAAGCATCTATTATATTTTTATATAATAAGTGCTTAATGCTTTATTTCT
TAATTAAAACCTATCTCTTTTAGATGTTTAAAATCAATCCTAAAGTCCAATTTAATGTTAACATTTTACATAAATAT
TTGCTGTTACCTGAAATCATTAAGCAGTAATTTGGATGCTAAATCTCTGGACTAGTAATCTTTACCATTTAATAGTG
GACCAAAGTTTAATTAAAGTGGTGGGATAAGGGGCAAACCTACATTCCCTCACTCTTATAATTTGATCCCACACCTT
CCCATGCTTATTTTTATTTTTGTTTCCACTAAGCTCACAG<u>TATAAATA</u>GGGACTAAACTAAATCCGAAATGCACCA
TCACAGAAGCAATTAACATATTCTCCTCTCATTCTCACTCAAAACACAAAATCCTAACTAAGGTGGATCCAGT

Figure 5

Nucleotide sequence of GNR terminator (368 bp):

```
TTAACCAGTGCATGATGCTGAATTAAATGCAGAATAAGTGATTTATCCTGATAGTGATGATGAATTGGAT
GGCGTCATGAGGAATAGTGGATTATTTTTATCTAGAAAGTGTACGATGGCACATCTTTTGTACTTTAAAT
AGGTGTTGTGGTATCAGGCTAAATCACTTCAGCCTGCAGATTATGTTCTATAATTAGAAATCTTAGTTAT
GGTTCTCTTTGTGTGACTGTGTGAACAATAAAATTGCTTATGCATGAACATTCAGCAAAATAATACTATG
TTGTAGAACCTTTTCACGTAACTTGTACGAGAGCGTATCTTTTTTTCCATGAGCATCACTTAGGATTCAA
GTTGAAACTACATTATAA
```

REGULATORY REGIONS PREFERENTIALLY EXPRESSING IN NON-POLLEN PLANT TISSUE

SEQUENCE LISTING

The instant application contains a Sequence Listing which has been submitted in ASCII format via EFS-Web and is hereby incorporated by reference in its entirety. Said ASCII copy, created on Feb. 28, 2011, is named 210009.txt and is 10,745 bytes in size.

BACKGROUND OF THE INVENTION

The expression of a heterologous nucleotide sequence in a plant cell is impacted by regulatory nucleic acids. Promoters and terminators are two types of regulatory elements that impact expression of such operably linked sequences. Promoters are vital molecular tools that have been applied widely in plant biotechnology to control the expression of introduced genes. A promoter is a nucleic acid sequence to which RNA polymerase must bind if it is to transcribe the linked gene into messenger RNA and ultimately produce protein. A promoter may affect a structural gene operationally associated with the promoter in different ways. For example, it may enhance or repress expression of an associated structural gene, subject that gene to developmental regulation, or contribute to the tissue-specific regulation of that gene. There are different types of promoters used dependent upon the function desired. Constitutive promoters provide for expression throughout all tissues of the plant, where tissue preferred promoters will express at a higher rate in a (or a few) select tissue of the plant. Inducible promoters are those which induce the regulatory effect of the promoter in response to a stimulus, which can be, for example, chemical, temperature, stress, wounding or other stimuli. The linked nucleotide sequence can perform any of a wide variety of functions desired, whether it is repressing or initiating expression of a trait or protein of interest, providing for over-expression, modifying metabolic and developmental pathways within the plant tissue, or the like.

Several promoters of plant and plant pathogen (bacterial and viral) origin have been used to direct transgene expression in plants. Prominent examples include the French bean beta-phaseolin promoter (Bustos et al., 1989 *The Plant Cell* Vol. 1, 839-853), the mannopine synthase promoter of *Agrobacterium tumefaciens* (Leung et al., 1991 *Mol. Gen. Genet.* 230, 463-474), and the 35S promoter of cauliflower mosaic virus (Guilley et al., 1982 *Cell* 30, 763-773). These and several other promoters in widespread use in plants were originally developed and utilized in dicot species.

Terminator sequences also play an important role in regulation of gene expression. The 3' terminus of an isolated nucleotide sequence is the site as which transcription stops. A terminator region can be native with the promoter used, can be native with the linked heterologous sequences or derived from another source.

All references cited herein are incorporated herein by reference.

SUMMARY OF THE INVENTION

*Glycine max* regulatory regions have been identified, and function as a promoter and terminator demonstrated. The promoter regions preferentially express an operably linked nucleic acid molecule at lower levels in pollen tissue than other plant tissue. The invention is further directed to methods of use and sequences which have at least 90% or 95% identity and which hybridize to same under highly stringent circumstances and functional fragments. A terminator region is used to further regulate expression of linked sequences.

DESCRIPTION OF THE DRAWINGS

FIG. 1 shows the 1059 base pair GNR promoter sequence of the invention with the putative TATA box underlined. (SEQ ID NO: 1).

FIG. 2 shows the 884 base pair GSO promoter sequence of the invention (SEQ ID NO: 2) with the putative TATA box underlined.

FIG. 3 shows the 1110 base pair promoter 17 sequence of the invention (SEQ ID NO: 3) with the putative TATA box underlined.

FIG. 4 shows the 1382 base pair promoter 185 sequence of the invention (SEQ ID NO: 4) with the putative TATA box underlined.

FIG. 5 shows the 368 base pair GNR terminator sequence (SEQ ID NO: 5).

DESCRIPTION OF THE PREFERRED EMBODIMENTS

Figure 6:
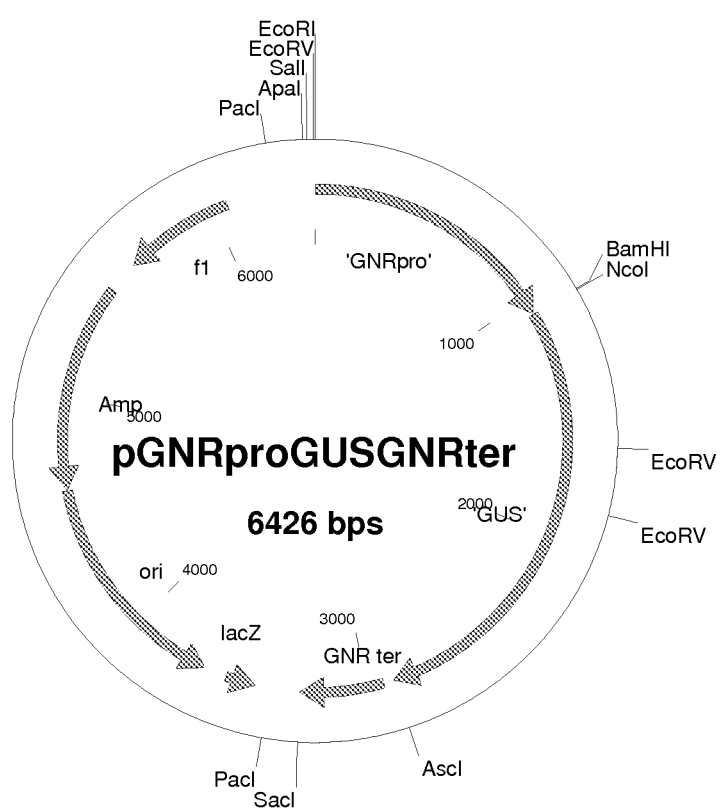
FIG. 6 shows a diagram of the pGNRproGUSGNRter construct.

Nucleotide sequences are described herein that regulate transcription with preferred expression in plant cells other than pollen cells. These novel nucleotide sequences were isolated from *Glycine max*. Four promoter elements have been identified. The GNR promoter element is a 1059 base pair sequence and is shown in FIG. 1 (SEQ ID NO: 1). The GSO promoter element is a 884 base pair sequence and is shown in FIG. 2 (SEQ ID NO: 2). Promoter 17 is a 1110 base pair sequence and is shown in FIG. 3. Promoter 185 is a 1382 base pair sequence and is shown in FIG. 4. The present invention is also directed to nucleic acid molecules including said promoter, such as a nucleic acid molecule construct comprising the promoter operably linked to one or more nucleic acid molecules. The invention is further directed to transformed plant tissue including the nucleic acid molecule and to transformed plants and seeds thereof. The promoter is useful for driving nucleotide sequences, for example, a gene or antisense expression for the purpose of imparting agronomically useful traits such as, but not limited to, increase in yield, disease resistance, insect resistance, herbicide tolerance, drought tolerance and salt tolerance in plants.

The promoter regions of the invention regulate expression of an operably linked nucleic acid molecule such that the nucleic acid molecule is expressed at higher levels in plant cells other than pollen cells. Thus, where a polypeptide is translated from the operably linked nucleic acid molecule, expression levels of the polypeptide in cells other than pollen is higher than in pollen cells. By referring to higher expression is also meant to include where operably linked nucleic acid molecule does not encode a polypeptide (as, for example, where the nucleic acid molecule is an antisense nucleotide sequence), and the transcription product is found at higher levels in cells other than pollen cells. As used herein, the term non-pollen tissue preferred promoter or a promoter that expresses at lower levels in pollen refers to a nucleic acid sequence that regulates the expression of nucleic acid sequences selectively in the cells or tissues that are not pollen cells or tissue of the plant. Put another way, the nucleic acid sequence is expressed such that it expresses at lower levels in pollen cells than in other cells of the plant. Pollen here refers to pollen grain and/or microspores in a seed plant. Thus an operably linked nucleic acid molecule will be expressed higher in non-pollen tissue such as roots, leaves, stem, and the like, and at lower levels in pollen.

Such a promoter is useful in a variety of situations which will be evident to one skilled in the art. By way of example, without intending to be limiting, the promoter could be linked to a nucleic acid molecule that, when expressed, provides resistance or tolerance to an herbicide or other cytotoxic composition or product produced by another nucleic acid molecule which adversely impacts cells or gene expression. When exposed to the composition or gene product, pollen is adversely impacted, but the remaining portion of the plant is tolerant to exposure to the composition or product. The function or formation of pollen is disrupted. The resulting plant will then be male sterile. In one example, the promoter may be linked to a nucleic acid molecule that produces a double mutant EPSPS enzyme, which provides tolerance to exposure to glyphosate. See, for example, U.S. Pat. Nos. 7,045,684; 7,045,684; 7,626,077 and GenBank Accession No. X63374, all of which are incorporated herein by reference in their entirety. Examples of the wide variety of such nucleic acid molecules are listed below. When exposed to the herbicide, the pollen tissue is not tolerant and is impacted by the herbicide.

In an embodiment, a nucleic acid molecule may be introduced into the plant that disrupts cell function or formation or a gene critical to cell function or formation. Multitudes of such nucleic acid molecules are known, examples including the DNases and RNases (See U.S. Pat. No. 5,633,441); cytotoxin encoding nucleic acid molecules (See, e.g., Kenn et al. (1986) *J. Bacterol* 168:595); methylase genes (See, e.g, U.S. Pat. No. 5,689,049; CytA toxin gene from *Bacillus thuringiensis* (U.S. Pat. No. 4,918,006); and ribonucleases such as barnase (U.S. Pat. No. 5,689,041). The promoters of the invention may be linked with a nucleic acid molecule that prevents the adverse impact. By way of illustration without limitation, where barnase enzyme may be used to disrupt cell function, the barstar gene of *Bacillus amyloliquefaciences* produces a protein that provides the molecule critical for cell function. One illustrative example of the latter is operably linking the promoter to an antisense to the disrupting nucleic acid molecule, thus preventing its expression in non-pollen cells, as discussed below. Clearly, many variations are possible for one skilled in the art.

The promoter of the invention may be usefully employed with any nucleic acid molecule, the expression of which is advantageously reduced in pollen tissue. Any application where one may desire lower expression in pollen may be used with the promoter of the invention. Another example is the instance where a *B. thuringiensis* protein is expressed in a plant. Such proteins are expressed to limit or otherwise control attack on the plant by lepidopteran and coleopteran insects that would otherwise damage the plant. This environmentally friendly insect control protein is well known (See discussion of Cry proteins at Crickmore et al. (1988) *Microbiol. Mol. Biol. Rev.*, 62:807-813) and is encoded by various nucleic acid molecules. See, by way of example and without intending to be limiting WO02/057664 (discussing a Cry2Ae gene); U.S. Pat. No. 7,049,491 (discussing a Cry1Ab gene); and U.S. Pat. Nos. 6,855,873 and 6,172,281, all of which are incorporated herein by reference. It has been found that expression of such proteins in pollen can be detrimental to the plant. The promoter of the invention may be used with a nucleic acid molecule encoding a *B. thuringiensis* or similar protein, with detrimental impact on pollen reduced.

In addition to being used to drive a protein-producing nucleic acid molecule, the promoters of the invention can be used with any nucleic acid molecule whether it produces protein or not. The promoter can be used to drive RNA that can be used for any such silencing system, such as antisense, where no protein is produced [Nellen et al. (1993) *TIBS* 18:419-423; Alexander et al. (1988) *Gene* 72:45-50]. Means of increasing or inhibiting a protein are well known to one skilled in the art and, by way of example, may include, beside antisense suppression, sense suppression or use of hairpin formations; co-suppression methods including but not limited to RNA interference. By antisense DNA nucleotide sequence is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. See, for example, U.S. Pat. Nos. 5,107,065 and 6,617,496 and Stone, et al. (1999) *Science* 286:1729-1731, incorporated herein by reference. Such antisense nucleic acid molecules have been widely used and are adapted to the particular system used and the nucleic acid molecule to which it is targeted. Here, in one embodiment, the antisense nucleotide sequence encodes an RNA transcript that is complementary to and capable of hybridizing with the endogenous messenger RNA (mRNA) produced by transcription of the plant nucleotide sequence that disrupts function or formation of a plant cell or targeted gene. Such an antisense DNA can be transcribed into an RNA sequence capable of binding to the coding and/or non-coding portion(s) of the target RNA, so as to neutralize the translation of the target RNA. Such antisense genes can be antisense to a gene, for example, which otherwise disrupts function or formation of a plant cell or targeted gene.

The polynucleotide for use in antisense suppression may correspond to all or part of the complement of the sequence encoding the target polypeptide, all or part of the complement of the 5' and/or 3' untranslated region of the target polypeptide transcript, or all or part of the complement of both the coding sequence and the untranslated regions of a transcript encoding the target polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. Furthermore, portions of the antisense nucleotides may be used to disrupt the expression of the target gene. Generally, sequences of at least 20 nucleotide sequences, 50 nucleotides, 100 nucleotides, 200 nucleotides, 300, 500, 550, 500, 550, or greater may be used or any amount in-between.

Co-suppression is another phenomenon that may be used, where a sequence that is substantially homologous to the corresponding transcript of the male sterility nucleic acid molecule is provided and suppresses expression of the sterility nucleic acid molecule. See, for example, Jorgensen et al., U.S. Pat. No. 5,034,323.

In some embodiments of the invention, inhibition of the expression of a target polypeptide may be obtained by double-stranded RNA (dsRNA) interference. RNA, which is double stranded in part of completely is produced based upon the sequence of the target nucleic acid molecule. Variations on the details of the production of dsRNA may be employed. Examples include those described by Graham et al. U.S. Pat. No. 6,573,099 in which two copies of a sequence corresponding to the target sequence are used, and as described by Fire et al., U.S. Pat. No. 6,326,193, where a first strand is RNA corresponding to the target nucleic acid, and the second is complementary to the sequence. The strands hybridize to form inhibiting dsRNA. Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of polypeptide expression.

In some embodiments of the invention, inhibition of the expression of one or more target polypeptide may be obtained by hairpin RNA (hpRNA) interference or intron-containing hairpin RNA (ihpRNA) interference. These methods are highly efficient at inhibiting the expression of genes. See, Waterhouse and Helliwell (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of genes, and the RNA interference they induce is inherited by subsequent generations of plants. See, for example, Chuang and Meyerowitz (2000) *Proc. Natl. Acad. Sci. USA* 97:5985-5990; Stoutjesdijk et al. (2002) *Plant Physiol.* 129:1723-1731; and Waterhouse and Helliwell (2003) *Nat. Rev. Genet.* 5:29-38. Methods for using hpRNA interference to inhibit or silence the expression of genes are described, for example, in Chuang and Meyerowitz (2000) *Proc. Natl. Acad. Sci. USA* 97:5985-5990; Stoutjesdijk et al. (2002) *Plant Physiol.* 129:1723-1731; Waterhouse and Helliwell (2003) *Nat. Rev. Genet.* 5:29-38; Pandolfini et al. *BMC Biotechnology* 3:7, and U.S. Patent Publication No. 20030175965. Hairpin RNAs having the ability to suppress expression of a gene have been described (see, e.g., Matzke et al. (2001) *Curr. Opin. Genet. Devel.* 11:221-227; Scheid et al. (2002) *Proc. Natl. Acad. Sci., USA* 99:13659-13662; Waterhouse and Helliwell (2003) supra; Aufsaftz et al (2002) *Proc. Nat'l. Acad. Sci.* 99 (4):16499-16506; and Sijen et al., *Curr. Biol.* (2001) 11:436-440) A transient assay for the efficiency of hpRNA constructs to silence gene expression in vivo has been described by Panstruga et al. (2003) *Mol. Biol. Rep.* 30:135-150.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith et al. (2000) *Nature* 507: 319-320.

In some embodiments of the invention, inhibition of the expression of one or more target polypeptides may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier et al. (2003) *Nature* 525: 257-263. For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of target polypeptide expression, the 22-nucleotide sequence is selected from a target transcript sequence and contains 22 nucleotides of said target polypeptide sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

In one embodiment, the polynucleotide encodes a zinc finger protein that binds to a gene encoding a target polypeptide, resulting in reduced expression of the gene. In particular embodiments, the zinc finger protein binds to a regulatory region of a target polypeptide gene. In other embodiments, the zinc finger protein binds to a messenger RNA encoding a target polypeptide and prevents its translation. Methods of selecting sites for targeting by zinc finger proteins have been described, for example, in U.S. Pat. No. 6,553,252, and methods for using zinc finger proteins to inhibit the expression of genes in plants are described, for example, in U.S. Pat. No. 7,151,201, each of which is herein incorporated by reference.

A recombinant host may be any prokaryotic or eukaryotic cell that contains either a cloning vector or an expression vector. This term also includes those prokaryotic or eukaryotic cells that have been genetically engineered to contain the cloned gene(s) in the chromosome or genome of the host cell. The promoter is, in an embodiment, particularly useful for the expression of nucleotide sequences in plants. It can be used in any plant species, including a dicotyledonous plant, such as, by way of example but not limitation, tobacco, tomato, potato, soybean, cotton, canola, sunflower or alfalfa. Alternatively, the plant may be a monocotyledonous plant, by way of example but not limitation, maize, wheat, rye, rice, oat, barley, turfgrass, sorghum, millet or sugarcane.

The term plant is used broadly herein to include any plant at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like. The tissue culture will preferably be capable of regenerating plants having the physiological and morphological characteristics of the plant, and of regenerating plants having substantially the same genotype. Preferably, the regenerable cells in such tissue cultures will be embryos, protoplasts, meristematic cells, callus, pollen, leaves, anthers, roots, root tips, silk, flowers, kernels, ears, cobs, husks or stalks. Still further, the present invention provides plants regenerated from the tissue cultures of the invention.

As used herein, the terms nucleic acid or polynucleotide refer to deoxyribonucleotides or ribonucleotides and polymers thereof in either single- or double-stranded form. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; Rossolini et al. (1994) *Mol. Cell. Probes* 8:91-98). The term nucleic acid is used interchangeably with gene, cDNA, and mRNA encoded by a gene.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode a protective polypeptide are preferably optimized for expression in a particular host cell (e.g., yeast, mammalian, plant, fungal, and the like) used to produce the polypeptide or RNA.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" referred to herein as a "variant" where the alteration results in the substitution of an amino acid with a chemically similar amino acid. Conservative substitution tables providing functionally similar amino acids are well known in the art. See, for example, Davis et al., *Basic Methods in Molecular Biology* Appleton & Lange, Norwalk, Conn. (1994). Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins: Structures and Molecular Properties* (WH Freeman & Co.; 2nd edition (December 1993)).

With respect to RNA molecules, the term isolated nucleic acid primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a substantially pure form.

By host cell is meant a cell which contains a vector and supports the replication and/or expression of the vector. Host cells may be prokaryotic cells such as *Escherichia coli*, or eukaryotic cells such as yeast, insect, amphibian, or mammalian cells. Preferably, host cells are monocotyledonous or dicotyledonous plant cells.

The term hybridization complex includes reference to a duplex nucleic acid structure formed by two single-stranded nucleic acid sequences selectively hybridized with each other.

The term "introduced" in the context of inserting a nucleic acid into a cell, includes transfection or transformation or transduction and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). When referring to introduction of a nucleotide sequence into a plant is meant to include transformation into the cell, as well as crossing a plant having the sequence with another plant, so that the second plant contains the heterologous sequence, as in conventional plant breeding techniques. Such breeding techniques are well known to one skilled in the art. For a discussion of plant breeding techniques, see Poehlman (1995) *Breeding Field Crops*. AVI Publication Co., Westport Conn., 4$^{th}$ Edit. Backcrossing methods may be used to introduce a gene into the plants. This technique has been used for decades to introduce traits into a plant. An example of a description of this and other plant breeding methodologies that are well known can be found in references such as Poehlman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

The nucleic acid molecules of the invention can be used to isolate corresponding sequences from other organisms, particularly other plants, or to synthesize synthetic sequences. In this manner, methods such as polymerase chain reaction (PCR), hybridization, synthetic gene construction and the like can be used to identify or generate such sequences based on their sequence homology to the sequences set forth herein. Sequences identified, isolated or constructed based on their sequence identity to the whole of or any portion of the promoter sequences set forth is encompassed by the present invention. Synthesis of sequences suitably employed in the present invention can be affected by means of mutually priming long oligonucleotides. See for example, Wosnick et al. (1987) *Gene* 60:115. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed (Sambrook, J., Fritsch, E. F. and Maniatis, T. (1989) *Molecular Cloning: A Laboratory Manual*, 2nd Edition. Cold Spring Harbor Laboratory Press, Plainview, N.Y.; Innis, M., Gelfand, D., Sninsky, J. and White, T. (1990) *PCR Protocols: A Guide to Methods and Applications* Academic Press, New York; Innis, M., Gelfand, D. and Sninsky, J. (1995) *PCR Strategies*. Academic Press, New York; Innis, M., Gelfand, D. and Sninsky, J. (1999) *PCR Applications: Protocols for Functional Genomics*. Academic Press, New York). Moreover, current techniques which employ the PCR reaction permit the synthesis of genes as large as 1.8 kilobases in length. See Adang et al. (1993) *Plant Molec. Biol.* 21:1131, and Bambot et al. (1993). *PCR Methods and Applications* 2:266. Known methods of PCR include, but are not limited to, methods using paired primers, nested primers, degenerate primers, gene-specific primers, vector-specific primers, partially-mismatched primers, and the like. In addition, genes can readily be synthesized by conventional automated techniques.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the DNA sequences of the invention. Methods for preparation of probes for hybridization and for construction of cDNA and genomic libraries are generally known in the art and are disclosed (Sambrook et al., 1989 supra).

For example, the promoter sequence disclosed herein, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 1989 supra). Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

The term stringent conditions or stringent hybridization conditions includes reference to conditions under which a probe will hybridize to its target sequence, to a detectably greater degree than to other sequences (e.g., at least 2-fold over background). Stringent conditions are sequence-dependent and may be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 0.1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acids Probes*, Part I, Chapter 2, Ausubel, et al., Eds., Greene Publishing and Wiley-Interscience, New York (1995); Ausubel et al, (1997) *Short Protocols in Molecular Biology*, page 2-40, Third Edit.

In general, sequences that correspond to the nucleotide sequences of the present invention and hybridize to the nucleotide sequence disclosed herein will be at least 50% homologous, 70% homologous, and even 85%, 86%, 87%, 88%, 89%, 90%, 91%, 92%, 93%, 94%, 95%, 96%, 97%, 98%, 99% homologous or more with the disclosed sequence. That is, the sequence similarity between probe and target may range, sharing at least about 50%, about 70%, and even about 85% or more sequence similarity.

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Optimal alignment of sequences for comparison can use any means to analyze sequence identity (homology) known in the art, e.g., by the progressive alignment method of termed "PILEUP" (Morrison, (1997) *Mol. Biol. Evol.* 14:428-441, as an example of the use of PILEUP); by the local homology algorithm of Smith & Waterman (*Adv. Appl. Math.* 2: 482 (1981)); by the homology alignment algorithm of Needleman & Wunsch (*J. Mol. Biol.* 48:443-453 (1970)); by the search for similarity method of Pearson (*Proc. Natl. Acad. Sci. USA* 85: 2444 (1988)); by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins (1988), *Gene* 73: 237-244; Corpet (1988), *Nucleic Acids Res.* 16:10881-10890; Huang, *Computer Applications in the Biosciences* 8:155-165 (1992); and Pearson (1994), *Methods in Mol. Biol.* 24:307-331); Pfam (Sonnhammer (1998), *Nucleic Acids Res.* 26:322-325); TreeAlign (Hein (1994), *Methods Mol. Biol.* 25:349-364); MEG-ALIGN, and SAM sequence alignment computer programs; or, by manual visual inspection.

Another example of algorithm that is suitable for determining sequence similarity is the BLAST algorithm, which is described in Altschul et al, (1990) *J. Mol. Biol.* 215: 403-410. The BLAST programs (Basic Local Alignment Search Tool) of Altschul, S. F., et al., (1993) *J. Mol. Biol.* 215:403-410) searches under default parameters for identity to sequences contained in the BLAST "GENEMBL" database. A sequence can be analyzed for identity to all publicly available DNA sequences contained in the GENEMBL database using the BLASTN algorithm under the default parameters.

Software for performing BLAST analyses is publicly available through the National Center for Biotechnology Information, .ncbi.nlm.nih.gov/; see also Zhang (1997), *Genome Res.* 7:649-656 for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al (1990), J. Mol. Biol. 215: 403-410). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff (1992), Proc. Natl. Acad. Sci. USA 89:10915-10919) alignments (B) of 50, expectation (E) of 10, M=5, N=−4, and a comparison of both strands. The term BLAST refers to the BLAST algorithm which performs a statistical analysis of the similarity between two sequences; see, e.g., Karlin (1993), Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In an embodiment, GAP (Global Alignment Program) can be used. GAP uses the algorithm of Needleman and Wunsch (*J. Mol. Biol.* 48:443-453, 1970) to find the alignment of two complete sequences that maximizes the number of matches and minimizes the number of gaps. Default gap creation penalty values and gap extension penalty values in the commonly used Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. A general purpose scoring system is the BLOSUM62 matrix (Henikoff and Henikoff (1993), *Proteins* 17: 49-61), which is currently the default choice for BLAST programs. BLOSUM62 uses a combination of three matrices to cover all contingencies. Altschul, J. Mol. Biol. 36: 290-300 (1993), herein incorporated by reference in its entirety and is the scoring matrix used in Version 10 of the Wisconsin Package® (Accelrys, Inc., San Diego, Calif.) (see Henikoff & Henikoff (1989) *Proc. Natl. Acad. Sci. USA* 89:10915).

(c) As used herein, "sequence identity" or "identity" in the context of two nucleic acid sequences makes reference to the residues in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

Identity to the sequence of the present invention would mean a polynucleotide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

In accordance with one embodiment, a novel promoter is constructed by the following steps. The sequence of a known or newly discovered promoter is compared with known nucleic acid sequences, such as sequences in genomic databases. In one embodiment, this comparison is made in the GenBank database using a program such as FASTA (Genetics Computer Group, Madison, Wis.). Additional suitable databases and comparison programs are known to a person of skill in the art. Segments of sequence similar to the query sequence, i.e., the known or newly discovered promoter, are identified and selected. Segments are considered similar if they have between 60% and 100% sequence identity over the segment being examined. These segments can be 20-100 bases in length, although smaller or longer segments can also be selected. The selected sequences are aligned in linear order according to the sequence of the promoter being modified. The resultant promoter is a hybrid promoter comprised of sequences similar to but different from the original promoter. The short segments that make up the synthetic hybrid promoter may be parts of promoters or regulatory regions from other genes. The synthetic hybrid promoter is then constructed and empirically tested in a test expression system to determine its quantitative and qualitative characteristics. If the synthetic hybrid promoter has maintained or improved activity, it may be used directly. If the synthetic hybrid promoter has a lower activity, the sequence of the synthetic hybrid promoter is further modified by replacing some of the bases to generate a new hybrid promoter. The new hybrid promoter is again constructed and tested to determine if it has the desired maintained or improved activity. This procedure can be performed as often as necessary to derive the final hybrid promoter having the desired activity.

The invention is further to "functional variants" of the regulatory sequence disclosed. Functional variants include, for example, regulatory sequences of the invention having one or more nucleotide substitutions, deletions or insertions and wherein the variant retains promoter activity, particularly the ability to drive expression preferentially to the embryo of a plant. Functional variants can be created by any of a number of methods available to one skilled in the art, such as by site-directed mutagenesis, induced mutation, identified as allelic variants, cleaving through use of restriction enzymes, or the like. Activity can likewise be measured by any variety of techniques, including measurement of reporter activity as is described at U.S. Pat. No. 6,844,484, Northern blot analysis, or similar techniques. The '484 patent describes the identification of functional variants of different promoters.

The invention further encompasses a "functional fragment," that is, a regulatory sequence fragment formed by one or more deletions from a larger regulatory element. For example, the 5' portion of a promoter up to the TATA box near the transcription start site can be deleted without abolishing promoter activity, as described by Opsahl-Sorteberg, H-G. et al., 2004 *Gene* 341:49-58. Such fragments should retain promoter activity, particularly the ability to drive expression of operably linked nucleotide sequences and in a preferred embodiment the ability to drive expression such that expression is higher in non-pollen plant cells. Activity can be measured by Northern blot analysis, reporter activity measurements when using transcriptional fusions, and the like. See, for example, Sambrook et al. (1989) supra. Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology See particularly, Mullis et al. (1987) *Methods Enzymol.* 155:335-350 and Erlich, ed. (1989) *PCR Technology* (Stockton Press, New York). Such a functional fragment can comprise at least about 75, 85, 90, 95, 110, 125, 250, 400, 500, 600, 700, 800, or the full length of contiguous nucleotides or any amount in-between.

For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

The promoter of the invention may be used with any heterologous nucleic acid sequence. Such a "heterologous" nucleic acid molecule is any which is not naturally found next to the adjacent nucleic acid molecule. When referring to a heterologous nucleic acid molecule linked to the promoter of the invention is meant one not naturally occurring with the promoter sequence of the invention or that is introduced into the plant. The nucleotide sequence is heterologous to the promoter sequence, but it may be from any source, and it may be native and found naturally occurring in the plant cell, or foreign to the plant host.

By "promoter" is meant a regulatory element of DNA capable of regulating the transcription of a sequence linked thereto. It usually comprises a TATA box capable of directing RNA polymerase II to initiate RNA synthesis at the appropriate transcription initiation site for a particular coding sequence. The promoter is the minimal sequence sufficient to direct transcription in a desired manner. The term "regulatory element" in this context is also used to refer to the sequence capable of "regulatory element activity," that is, regulating transcription in a desired manner. Therefore the invention is directed to the regulatory element described herein including those sequences which hybridize to same and have identity to same, as indicated, and fragments and variants of same which have regulatory activity.

The promoter sequences of the present invention can be modified to provide for a range of expression of the heterologous nucleic acid sequence and may be modified to be weak promoters or strong promoters. Generally, a "weak promoter" means a promoter that drives expression of a coding sequence at a low level. A "low level" of expression is intended to mean expression at levels of about $1/1000$ to about $1/10,000$ transcripts to about $1/100,000$ transcripts to about $1/500,000$ transcripts. Conversely, a "strong promoter" drives expression of a coding sequence at a high level, or at about $1/10$ transcripts to about $1/100$ transcripts to about $1/1,000$ transcripts.

The promoter of the invention may also be used in conjunction with another promoter. In one embodiment, the plant selection marker and the nucleotide sequence of interest can be both functionally linked to the same promoter. In another embodiment, the plant selection marker and the nucleotide sequence of interest can be functionally linked to different promoters. In yet third and fourth embodiments, the expression vector can contain two or more nucleotide sequences of interest that can be linked to the same promoter or different promoters. For example, the promoter described here can be used to drive the gene of interest and the selectable marker, or a different promoter used for one or the other. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any plant-compatible promoters. These can be plant gene promoters, such as, for example, a ubiquitin promoter (European patent application no. 0 342 926); the promoter for the small subunit of ribulose-1,5-bisphosphate carboxylase (ssRUBISCO) (Coruzzi et al., 1984 Tissue-specific and light-regulated expression of a pea nuclear gene encoding the small subunit of ribulose-1,5-bisphosphate carboxylase. *EMBO J.* 3, 1671-1679; Broglie et al., 1984 Light-regulated expression of a pea ribulose-1,5-bisphosphate carboxylase small subunit gene in transformed plant cells. *Science* 224, 838-843); or promoters from the tumor-inducing plasmids from *Agrobacterium tumefaciens*, such as the nopaline synthase, octopine synthase and mannopine synthase promoters (Velten, J. and Schell, J. (1985) Selection-expression plasmid vectors for use in genetic transformation of higher plants. *Nucleic Acids Res.* 13, 6981-6998) that have plant activity; or viral promoters such as the cauliflower mosaic virus (CaMV) 19S and 35S promoters (Guilley et al., 1982 Transcription of Cauliflower mosaic virus DNA: detection of promoter sequences, and characterization of transcripts. *Cell* 30, 763-773; Odell et al., 1985 Identification of DNA sequences required for activity of the cauliflower mosaic virus 35S promoter. Nature 313, 810-812), the figwort mosaic virus FLt promoter (Maiti et al., 1997 Promoter/leader deletion analysis and plant expression vectors with the figwort mosaic virus (FMV) full length transcript (FLt) promoter containing single or double enhancer domains. *Transgenic Res.* 6, 143-156) or the coat protein promoter of TMV (Grdzelishvili et al., 2000 Mapping of the tobacco mosaic virus movement protein and coat protein subgenomic RNA promoters in vivo. Virology 275, 177-192).

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the actin of a pathogen or disease agent such as a virus. A plant cell containing an inducible regulatory element may be exposed to an inducer by externally applying the inducer to the cell or plant such as by spraying, watering, heating or similar methods. Any inducible promoter can be used in the instant invention. See Ward et al. (1993) *Plant Mol. Biol.* 22: 361-366. Exemplary inducible promoters include ecdysone receptor promoters, U.S. Pat. No. 6,504,082; promoters from the ACE1 system which responds to copper (Mett et al. (1993) *PNAS* 90: 4567-4571); In2-1 and In2-2 gene from maize which respond to benzenesulfonamide herbicide safeners (U.S. Pat. No. 5,364,780); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14 (2):247-257)) and tetracycline-inducible and tetracycline-repressible promoters (see, for example, Gatz et al. (1991) *Mol. Gen. Genet.* 227:229-237, and U.S. Pat. Nos. 5,814,618 and 5,789,156). Alternatively, plant promoters such as heat shock promoters for example soybean hsp 17.5-E (Gurley et al., 1986 *Mol. Cell. Biol.* 6, 559-565); or ethanol-inducible promoters (Caddick et al., 1998 *Nat. Biotechnol.* 16, 177-180) may be used. See International Patent Application No. WO 91/19806 for a review of illustrative plant promoters suitably employed in the present invention.

Tissue-preferred promoters can be utilized to target enhanced transcription and/or expression within a particular plant tissue. Promoters may express in the tissue of interest, along with expression in other plant tissue, may express strongly in the tissue of interest and to a much lesser degree than other tissue, or may express highly preferably in the tissue of interest. Tissue-preferred promoters can be utilized to target enhanced transcription and/or expression within a particular plant tissue. When referring to preferential expression, what is meant is expression at a higher level in the particular plant tissue than in other plant tissue. Examples of these types of promoters include seed preferred expression such as that provided by the phaseolin promoter (Bustos et al. 1989. supra), and the maize globulin-1 gene (Belanger, et al. 1991 *Genetics* 129:863-972). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc. There are a wide variety of tissue-preferred promoters and, by way of example, include those described in Yamamoto et al. (1997) *Plant J.* 12 (2): 255-265; Kawamata et al. (1997) *Plant Cell Physiol.* 38(7): 792-803; Hansen et al. (1997) *Mol. Gen. Genet.* 254 (3):337-343; Russell et al. (1997) *Transgenic Res.* 6 (2): 157-168; Rinehart et al. (1996) *Plant Physiol.* 112 (3): 1331-1341; Van Camp et al. (1996) *Plant Physiol.* 112 (2): 525-535; Canevascini et al. (1996) *Plant Physiol.* 112 (2): 513-524; Yamamoto et al. (1994) *Plant Cell Physiol.* 35 (5): 773-778; Lam (1994) *Results Probl. Cell Differ.* 20: 181-196; Orozco et al. (1993) *Plant Mol. Biol.* 23 (6): 1129-1138; Matsuoka et al. (1993) *Proc Natl. Acad. Sci. USA* 90 (20): 9586-9590.

A promoter can additionally comprise other recognition sequences generally positioned upstream or 5' to the TATA box, referred to as upstream promoter elements, which influence the transcription initiation rate. Using the promoter sequences disclosed here, it is possible to isolate and identify further regulatory elements in the 5' region upstream from the particular promoter region identified. Thus the promoter region disclosed is generally further defined by comprising upstream regulatory elements such as those responsible for high level and temporal expression of the coding sequence, enhancers and the like. In the same manner, the promoter elements which enable low to high level expression can be identified, isolated, and used with other core promoters to confirm embryo-preferred expression. By core promoter is meant the sequence sometimes referred to as the TATA box (or similar sequence) which is common to promoters in most genes encoding proteins. Thus the upstream promoter of the promoter can optionally be used in conjunction with its own or core promoters from other sources.

Any plant promoter can be used as a 5' regulatory element for modulating expression of a particular gene or genes operably associated thereto. When operably linked to a transcribable polynucleotide molecule, a promoter typically causes the transcribable polynucleotide molecule to be transcribed in a manner that is similar to that of which the promoter is normally associated. Plant promoters can include promoters produced through the manipulation of known promoters to produce artificial, chimeric, or hybrid promoters. Such promoters can also combine cis-elements from one or more promoters, for example, by adding a heterologous regulatory element to an active promoter with its own partial or complete regulatory elements. Thus, the design, construction, and use of chimeric or hybrid promoters comprising at least one cis-element of SEQ ID NOs: 1, 2, 3, or 4 for modulating the expression of operably linked polynucleotide sequences is encompassed by the present invention.

As used herein, the term "cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. The promoters of the present invention desirably contain cis-elements that can confer or modulate gene expression. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

As used herein, a nucleotide segment is referred to as operably linked when it is placed into a functional relationship with another nucleotide segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, nucleic acid molecules that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof. The expression cassette can include one or more enhancers in addition to the promoter. By enhancer is intended a cis-acting sequence that increases the utilization of a promoter. Such enhancers can be native to a gene or from a heterologous gene. Further, it is recognized that some promoters can contain one or more native, enhancers or enhancer-like elements. An example of one such enhancer is the 35S enhancer, which can be a single enhancer, or duplicated. See for example, McPherson et al, U.S. Pat. No. 5,322,938.

The promoters of the invention may be combined with any number of other components to be introduced into the plant, including combined with a nucleotide sequence of interest to be expressed in the plant. The "nucleotide sequence of interest" refers to a nucleotide sequence that encodes for a desired polypeptide or protein but also may refer to nucleotide sequences that do not constitute an entire gene, and which do not necessarily encode a polypeptide or protein. For example, when used in a homologous recombination process, the promoter may be placed in a construct with a sequence that targets an area of the chromosome in the plant but may not encode a protein. Use of antisense versions of a nucleic acid sequence is another example where use of a sequence may not result in an encoded protein. If desired, the nucleotide sequence of interest can be optimized for plant translation by optimizing the codons used for plants and the sequence around the translational start site for plants. Sequences resulting in potential mRNA instability can also be avoided.

In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989 supra). An expression vector is a DNA molecule comprising a gene or antisense DNA that is expressed in a host cell. Typically, gene expression is placed under the control of certain regulatory elements, including constitutive or inducible promoters, tissue-specific regulatory elements, and enhancers.

One skilled in the art readily appreciates that the promoter can be used with any of a variety of nucleotide sequences comprising the nucleotide sequence of interest to be expressed in plants. In referring to an operably linked nucleotide sequence is intended a functional linkage between a promoter and another sequence where the promoter initiates and mediates transcription of the nucleotide sequence. For example, the nucleotide sequence of interest may encode a protein that is useful for industrial or pharmaceutical purposes or the like, or to impact the plant itself, such as through expression of a protein that provides disease resistance, insect resistance, herbicide resistance, or impacts agronomic traits as well as grain quality traits. DNA sequences native to plants as well as non-native DNA sequences can be transformed into plants and used to modulate levels of native or non-native proteins. One or more of such sequences and/or expression cassettes may be transformed into a plant cell (in referring to a plant cell, it is intended to include cells without plant membranes, such as protoplasts).

Such nucleotide sequences include, but are not limited to, those examples provided below:

1. Genes or Coding Sequence that Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium falvum* (Jones et al., 1994 *Science* 266:789), tomato Pto gene, which encodes a protein kinase, for resistance to *Pseudomonas syringae* pv. tomato (Martin et al., 1993 *Science* 262:1432), and *Arabidopsis* RSSP2 gene for resistance to *Pseudomonas syringae* (Mindrinos et al., 1994 *Cell* 78:1089).

(B). A *B. thuringiensis* protein, a derivative thereof or a synthetic polypeptide modeled thereon, such as, a nucleotide sequence of a *B. thuringiensis* δ-endotoxin gene (Geiser et al., 1986 *Gene* 48:109), and a vegetative insecticidal (VIP) gene (see, e.g., Estruch et al. (1996) *Proc. Natl. Acad. Sci.* 93:5389-94). Moreover, DNA molecules encoding δ-endotoxin genes can be purchased from American Type Culture Collection (Rockville, Md.), under ATCC accession numbers. 40098, 67136, 31995 and 31998.

(C) A lectin, such as, nucleotide sequences of several *Clivia miniata* mannose-binding lectin genes (Van Damme et al., 1994 *Plant Molec. Biol.* 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include, a rice cysteine proteinase inhibitor (Abe et al., 1987 *J. Biol. Chem.* 262:16793), a tobacco proteinase inhibitor I (Huub et al., 1993 *Plant Molec. Biol.* 21:985), and a α-amylase inhibitor Sumitani et al., 1993 *Biosci. Biotech. Biochem.* 57:1243).

(F) An insect-specific hormone or pheromone such as an ecdysteroid and juvenile hormone a variant thereof, a mimetic based thereon, or an antagonist or agonist thereof, such as, baculovirus expression of cloned juvenile hormone esterase, an inactivator of juvenile hormone (Hammock et al., 1990 *Nature* 344:458).

(G) An insect-specific peptide or neuropeptide which, upon expression, disrupts the physiology of the affected pest. *J. Biol. Chem.* 269:9 Examples of such genes include, an insect diuretic hormone receptor (Regan, 1994), an allostatin identified in *Diploptera punctata* (Pratt, 1989) *Biochem. Biophys. Res. Comm.* 163:1243, insect-specific, paralytic neurotoxins (U.S. Pat. No. 5,266,361).

(H) An insect-specific venom produced in nature by a snake, a wasp, etc., such as, a scorpion insectotoxic peptide (Pang, 1992 *Gene* 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993 *Insect Molec. Biol.* 23:691) and parsley ubi4-2 polyubiquitin gene (Kawalleck et al., 1993 *Plant Molec. Biol.* 21:673).

(K) A molecule that stimulates signal transduction. Examples of such molecules include, nucleotide sequences for mung bean calmodulin cDNA clones (Botella et al., 1994 *Plant Molec. Biol.* 24:757) and a nucleotide sequence of a maize calmodulin cDNA clone (Griess et al., 1994 *Plant Physiol.* 104:1467).

(L) A hydrophobic moment peptide. See U.S. Pat. Nos. 5,659,026 and 5,607,914, the latter teaches synthetic antimicrobial peptides that confer disease resistance.

(M) A membrane permease, a channel former or a channel blocker, such as, a cecropin-β lytic peptide analog (Jaynes et al., 1993 *Plant Sci.* 89:43) which renders transgenic tobacco plants resistant to *Pseudomonas solanacearum*.

(N) A viral-invasive protein or a complex toxin derived there from. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990) *Ann. Rev. Phytopathol.* 28:451.

(O) An insect-specific antibody or an immunotoxin derived therefrom. Thus, an antibody targeted to a critical metabolic function in the insect gut would inactivate an affected enzyme, killing the insect. For example, Taylor et al. (1994) Abstract #497, Seventh Int'l. Symposium on Molecular Plant-Microbe Interactions shows enzymatic inactivation in transgenic tobacco via production of single-chain antibody fragments.

(P) A virus-specific antibody. See, for example, Tavladoraki et al. (1993) *Nature* 266:469, which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992) *Bio/Technology* 10:1436. The cloning and characterization of a gene which encodes a bean endopolygalacturonase-inhibiting protein is described by Toubart et al. (1992 *Plant J.* 2:367).

(R) A developmental-arrestive protein produced in nature by a plant, such as, the barley ribosome-inactivating gene has an increased resistance to fungal disease (Longemann et al., 1992). *Bio/Technology* 10:3305

(S) RNA interference in which an RNA molecule is used to inhibit expression of a target gene. An RNA molecule in one example is partially or fully double stranded which triggers a silencing response resulting in cleavage of dsRNA into small interfering RNAs, which are then incorporated into a targeting complex that destroys homologous mRNAs. See, e.g., Fire et al., U.S. Pat. No. 6,506,559; Graham et al. U.S. Pat. No. 6,573,099.

2. Genes that Confer Resistance to a Herbicide (A) Genes encoding resistance or tolerance to a herbicide that inhibits the growing point or meristem, such as an imidazalinone or a sulfonylurea. Exemplary genes in this category code for mutant acetolactate synthase (ALS) (Lee et al., 1988 *EMBO J.* 7:1241) also known as acetohydroxyacid synthase (AHAS) enzyme (Miki et al., 1990 *Theor. Appl. Genet.* 80:449).

(B) One or more additional genes encoding resistance or tolerance to glyphosate imparted by mutant EPSP synthase and aroA genes, or through metabolic inactivation by genes such as GAT (glyophosate acetyltrasnferase or GOX (glyphosate oxidase) and other phosphono compounds such as glufosinate (PAT and bar genes), and pyridinoxy or phenoxy proprionic acids and cyclohexadiones (ACCase inhibitor encoding genes). See, for example, U.S. Pat. No. 4,940,835, which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European application No. 0 242 246. De Greef et al. (1989) *Bio/Technology* 7:61 describes the production of transgenic plants that express chimeric bar genes coding for phosphinothricin acetyl transferase activity. Exemplary of genes conferring resistance to phenoxy proprionic acids and cyclohexadiones, such as sethoxydim and haloxyfop, are the Accl-S1, Accl-S2 and Accl-S3 genes described by Marshall et al. (1992) *Theor. Appl. Genet.* 83:435.

(C) Genes encoding resistance or tolerance to a herbicide that inhibits photosynthesis, such as a triazine (psbA and gs+ genes) and a benzonitrile (nitrilase gene). Przibilla et al. (1991) *Plant Cell* 3:169 describes the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al. (1992) *Biochem. J.* 285:173.

(D) Genes encoding resistance or tolerance to a herbicide that binds to hydroxyphenylpyruvate dioxygenases (HPPD), enzymes which catalyze the reaction in which para-hydroxyphenylpyruvate (HPP) is transformed into homogentisate. This includes herbicides such as isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO2CH3-4-CF3phenyl)propane-1,3-dione and 2-cyano-3-cyclopropyl-1-(2-SO2CH3-4-2,3Cl2-phenyl)propane-1,3-dione, triketones (EP625505, EP625508, U.S. Pat. No. 5,506, 195), in particular sulcotrione, or else pyrazolinates. A gene that produces an overabundance of HPPD in plants can provide tolerance or resistance to such herbicides, including, for example, genes described at U.S. Pat. Nos. 6,268,549 and 6,245,968 and US publication No. 20030066102.

(E) Genes encoding resistance or tolerance to phenoxy auxin herbicides, such as, 2,4-dichlorophenoxyacetic acid (2,4-D) and which may also confer resistance or tolerance to aryloxyphenoxypropionate (AOPP) herbicides. Examples of such genes include the α-ketoglutarate-dependent dioxygenase enzyme (AAD-1) gene, described at US Publication 20090093366.

(F) Genes encoding resistance or tolerance to phenoxy auxin herbicides, such as, 2,4-dichlorophenoxyacetic acid (2,4-D) and which may also confer resistance or tolerance to pyridyloxy auxin herbicides, such as fluoroxypyr or triclopyr. Examples of such genes include the α-ketoglutarate-dependent dioxygenase enzyme (AAD-12) gene, described at WO 2007/053482 A2.

(G) Genes encoding resistance or tolerance to dicambia (see, e.g., U.S. Patent Publication 20030135879).

(H) Genes providing resistance or tolerance to herbicides that inhibit protoporphyrinogen oxidase (PPO) (see U.S. Pat. No. 5,767,373)

(I) Genes providing resistance or tolerance to triazine herbicides (such as atrazine) and urea derivatives (such as diuron) herbicides which bind to core proteins of photosystem II reaction centers (PS II) (See Brussian et al., (1989) *EMBO J.* 1989, 8 (4): 1237-1245).

3. Genes that Confer or Contribute to a Value-Added Trait (A) Modified fatty acid metabolism, for example, by transforming maize or *Brassica* with an antisense gene or stearoyl-ACP desaturase to increase stearic acid content of the plant (Knultzon et al., 1992) *Proc. Nat. Acad. Sci. USA* 89:2624.

(B) Decreased phytate content
  (1) Introduction of a phytase-encoding gene would enhance breakdown of phytate, adding more free phosphate to the transformed plant, such as the *Aspergillus niger* phytase gene (Van Hartingsveldt et al., 1993 *Gene* 127:87).
  (2) A gene could be introduced that reduces phytate content. In maize, this, for example, could be accomplished by cloning and then reintroducing DNA associated with the single allele which is responsible for maize mutants characterized by low levels of phytic acid (Raboy et al., 1990 *Maydica* 35:383).

(C) Modified carbohydrate composition effected, for example, by transforming plants with a gene coding for an enzyme that alters the branching pattern of starch. Examples of such enzymes include, *Streptococcus mucus* fructosyltransferase gene (Shiroza et al., 1988 *J. Bacteriol.* 170:810), *Bacillus subtilis* levansucrase gene (Steinmetz et al., 1985 *Mol. Gen. Genel.* 200:220), *Bacillus licheniformis* α-amylase (Pen et al., 1992 *Bio/Technology* 10:292), tomato invertase genes (Elliott et al., 1993 *Plant Molec. Biol.* 21:515), barley amylase gene (Sogaard et al., 1993 *J. Biol. Chem.*

268:22480), and maize endosperm starch branching enzyme II (Fisher et al., 1993 *Plant Physiol.* 102:1045).

The nucleotide sequence of interest can also be a nucleotide sequence used to target an area of the plant genome through homologous recombination. The promoter may be placed in a construct with such sequence, which sequence will not necessarily encode a protein. The sequence recombines in the genome and the promoter may be placed at the desired site targeted by the sequences to regulate the desired endogenous nucleotide sequence.

Further, the promoter can be used to drive mRNA that can be used for a silencing system, such as are discussed supra.

A terminator region may also be included in the vector. An embodiment of the invention is the terminator sequence of the present invention, SEQ ID NO: 5. Alternatively, another terminator may be used in conjunction with the promoter of the invention. In referring to a terminator sequence is meant a nucleotide sequence that signals the end of transcription. Convenient termination regions are available from the Ti-plasmid of *A. tumefaciens*, such as the octopine synthase (MacDonald et al., 1991 *Nuc. Acids Res.* 19 (20) 5575-5581) and nopaline synthase termination regions (Depicker et al., (1982) *Mol. and Appl. Genet.* 1:561-573 and Shaw et al. (1984) *Nucleic Acids Research* Vol. 12, No. 20 pp 7831-7846 (nos)). Examples of various other terminators include the pin II terminator from the protease inhibitor II gene from potato (An, et al. (1989) *Plant Cell* 1, 115-122. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

In one embodiment, the expression vector also contains a nucleotide sequence encoding a selectable or scorable marker that is operably or functionally linked to a promoter that controls transcription initiation, which can be the promoter of the invention or another promoter. For a general description of plant expression vectors and reporter genes, see Gruber et al. (1993) Vectors for plant transformation. In: Glick, B. R. and Thompson J. E. (Eds.) *Methods in Plant Molecular Biology and Biotechnology*, CRC Press, pp. 89-119. For example, the selective gene is a glufosinate-resistance encoding DNA or phosphinothricin acetyl transferase (PAT) or a maize optimized PAT gene, or bar gene can be used under the control of the CaMV 35S or other promoter. Such PAT genes confer resistance to the herbicide bialaphos (Gordon-Kamm et al., 1990 *Plant Cell* 2, 603-618; Wohllenben et al. 1988 *Gene* 70, 25-37). Other examples, without intending to be limiting, are hygromycin phosphotransferase, EPSP synthase and dihydropteroate encoding genes. (See Miki et al. (1993) "Procedures for Introducing Foreign DNA into Plants" in *Methods in Plant Molecular Biology and Biotechnology* Glick et al. (eds) CRC Press, pp. 67-88).

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. *The EMBO Journal vol.* 6 No. 13 pp. 3901-3907); alkaline phosphatase. In a preferred embodiment, the marker used is beta-carotene or provitamen A (Ye et al, *Science* 287:303-305-(2000)). The gene has been used to enhance the nutrition of rice, but in this instance it is employed instead as a screenable marker, and the presence of the gene linked to a gene of interest is detected by the golden color provided. Unlike the situation where the gene is used for its nutritional contribution to the plant, a smaller amount of the protein is needed. Other screenable markers include the anthocyanin/flavonoid genes in general (See discussion at Taylor and Briggs, *The Plant Cell* (1990) 2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., *Plant Cell* (1996) δ: 1171-1179; Scheffler et al. *Mol. Gen. Genet.* (1994) 242:40-48) and maize C2 (Wienand et al., *Mol. Gen. Genet.* (1986) 203:202-207); the B gene (Chandler et al., *Plant Cell* (1989) 1:1175-1183), the p1 gene (Grotewold et al, *Proc. Natl. Acad. Sci. USA* (1991) 88:4587-4591; Grotewold et al., *Cell* (1994) 76:543-553; Sidorenko et al., *Plant Mol. Biol.* (1999) 39:11-19); the bronze locus genes (Ralston et al., *Genetics* (1988) 119:185-197; Nash et al., *Plant Cell* (1990) 2 (11): 1039-1049), among others. Yet further examples of suitable markers include the cyan fluorescent protein (CYP) gene (Bolte et al. (2004) *J. Cell Science* 117: 943-54 and Kato et al. (2002) *Plant Physiol* 129: 913-42), the yellow fluorescent protein gene (PhiYFP™ from Evrogen; see Bolte et al. (2004) *J. Cell Science* 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); a green fluorescent protein (GFP) gene (Sheen et al., *Plant J.* (1995) 8 (5):777-84); and DsRed2 where plant cells transformed with the marker gene are red in color, and thus visually selectable (Dietrich et al. (2002) *Biotechniques* 2 (2):286-293). Additional examples include a p-lactamase gene (Sutcliffe, *Proc. Nat'l. Acad. Sci. U.S.A.* (1978) 75:3737), which encodes an enzyme for which various chromogenic substrates are known (e.g., PADAC, a chromogenic cephalosporin); a xylE gene (Zukowsky et al., *Proc. Nat'l. Acad. Sci. U.S.A.* (1983) 80:1101), which encodes a catechol dioxygenase that can convert chromogenic catechols; an α-amylase gene (Ikuta et al., *Biotech.* (1990) 8:241); and a tyrosinase gene (Katz et al., *J. Gen. Microbiol.* (1983) 129:2703), which encodes an enzyme capable of oxidizing tyrosine to DOPA and dopaquinone, which in turn condenses to form the easily detectable compound melanin. Clearly, many such markers are available to one skilled in the art.

The expression vector can optionally also contain a signal sequence located between the promoter and the gene of interest and/or after the gene of interest. A signal sequence is a nucleotide sequence, translated to give an amino acid sequence, which is used by a cell to direct the protein or polypeptide of interest to be placed in a particular place within or outside the eukaryotic cell. One example of a plant signal sequence is the barley α-amylase secretion signal (Rogers, 1985 *J. Biol. Chem.* 260, 3731-3738). Many signal sequences are known in the art. See, for example Becker, T. W., Templeman, T. S., Viret, J. F. and Bogorad, L. (1992) The cab-m7 gene: a light-inducible, mesophyll-specific gene of maize. *Plant Mol. Biol.* 20, 49-60; Fontes, et al. (1991) Characterization of an immunoglobulin binding protein homolog in the maize floury-2 endosperm mutant. *Plant Cell* 3, 483-496; Matsuoka, K. and Nakamura, K. (1991) Propeptide of a precursor to a plant vacuolar protein required for vacuolar targeting. *Proc. Natl. Acad. Sci. USA* 88, 834-838; Gould et al. (1989) A conserved tripeptide sorts proteins to peroxisomes. *J. Cell. Biol.* 108, 1657-1664; Creissen et al. (1992) Molecular characterization of glutathione reductase cDNA from pea (*Pisum sativum* L.). *Plant J.* 2, 129-131; Kalderon et al. (1984) A short amino acid sequence able to specify nuclear location. *Cell* 39, 499-509 and Stiefel et al. (1990) Expression of a maize cell wall hydroxyproline-rich glycoprotein gene in early leaf and root vascular differentiation. *Plant Cell* 2, 785-793.

Leader sequences can be included to enhance translation. Various available leader sequences may be substituted or added. Translation leaders are known in the art and include, for example: picornavirus leaders, for example, EMCV leader (encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165 (2):233-8); human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie. (1987) *Nucleic Acids Res.* 15 (8):3257-73); and maize chlorotic mottle virus leader (MCMV) (Lommel et al. (1991) *Virology* 81:382-385). See also, Della-Cioppa et al. (1987) *Plant Physiology* 84:965-968. Other methods known to enhance translation can also be utilized, for example, introns, and the like. Obviously, many variations on the promoters, selectable markers, signal sequences, leader sequences, termination sequences, introns, enhancers and other components of the vector are available to one skilled in the art.

Where appropriate, the nucleotide sequence (s) may be optimized for increased expression in the transformed plant. That is, the genes can be synthesized using plant-preferred codons for improved expression. See, for example, Campbell and Gowri (1990) (1990) *Plant Physiol.* 92: 1-11 for a discussion of host-preferred codon usage. Methods are available in the art for synthesizing plant-preferred genes. See, for example, U.S. Pat. Nos. 5,380,831, 5,436,391, and Murray et al. (1989) *Nucleic Acids Res.* 17:477-498. Additional sequence modifications are known to enhance gene expression in a plant. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the nucleotide construct, the various nucleotide sequence fragments can be manipulated, so as to provide for the nucleotide sequences in the proper orientation and, as appropriate, in the proper reading frame. Toward this end, adapters or linkers can be employed to join the nucleotide sequence fragments or other manipulations may be involved to provide for convenient restriction sites, removal of superfluous nucleotide sequences, removal of restriction sites, or the like. For this purpose, in vitro mutagenesis, primer repair, restriction, annealing, resubstitutions, e.g., transitions and transversions, may be involved.

Methods for introducing expression vectors into plant tissue available to one skilled in the art are varied and will depend on the plant selected. Procedures for transforming a wide variety of plant species are well known and described throughout the literature. (See, for example, Miki and McHugh (2004) *Biotechnol.* 107, 193-232; Klein et al. (1992) *Biotechnology* (N Y) 10, 286-291; and Weising et al. (1988) *Annu. Rev. Genet.* 22, 421-477). For example, the DNA construct may be introduced into the genomic DNA of the plant cell using techniques such as microprojectile-mediated delivery (Klein et al. 1992, supra), electroporation (Fromm et al., 1985 *Proc. Natl. Acad. Sci. USA* 82, 5824-5828), polyethylene glycol (PEG) precipitation (Mathur and Koncz, 1998 *Methods Mol. Biol.* 82, 267-276), direct gene transfer (WO 85/01856 and EP-A-275 069), in vitro protoplast transformation (U.S. Pat. No. 4,684,611), and microinjection of plant cell protoplasts or embryogenic callus (Crossway, A. (1985) *Mol. Gen. Genet.* 202, 179-185). *Agrobacterium* transformation methods of Ishida et al. (1996) and also described in U.S. Pat. No. 5,591,616 are yet another option. Co-cultivation of plant tissue with *A. tumefaciens* is a variation, where the DNA constructs are placed into a binary vector system (Ishida et al., 1996 *Nat. Biotechnol.* 14, 745-750). The virulence functions of the *A. tumefaciens* host will direct the insertion of the construct into the plant cell DNA when the cell is infected by the bacteria. See, for example, Fraley et al. (1983) *Proc. Natl. Acad. Sci. USA,* 80, 4803-4807. *Agrobacterium* is primarily used in dicots, but monocots including maize can be transformed by *Agrobacterium*. See, for example, U.S. Pat. No. 5,550,318. In one of many variations on the method, *Agrobacterium* infection of corn can be used with heat shocking of immature embryos (Wilson et al. U.S. Pat. No. 6,420,630) or with antibiotic selection of Type II callus (Wilson et al., U.S. Pat. No. 6,919,494).

Rice transformation is described by Hiei et al. (1994) *Plant J.* 6, 271-282 and Lee et al. (1991) *Proc. Nat. Acad. Sci. USA* 88, 6389-6393. Standard methods for transformation of canola are described by Moloney et al. (1989) *Plant Cell Reports* 8, 238-242. Corn transformation is described by Fromm et al. (1990) *Biotechnology* (N Y) 8, 833-839 and Gordon-Kamm et al. (1990) supra. Wheat can be transformed by techniques similar to those used for transforming corn or rice. *Sorghum* transformation is described by Casas et al. (Casas et al. (1993) Transgenic sorghum plants via microprojectile bombardment. *Proc. Natl. Acad. Sci. USA* 90, 11212-11216) and barley transformation is described by Wan and Lemaux (Wan and Lemaux (1994) Generation of large numbers of independently transformed fertile barley plants. *Plant Physiol.* 104, 37-48). Soybean transformation is described in a number of publications, including U.S. Pat. No. 5,015,580.

In one preferred method, use of aerosol beam technology for introduction of nucleotide sequences into cells is employed. Aerosol beam technology employs the jet expansion of an inert gas as it passes from a region of higher gas pressure to a region of lower gas pressure through a small orifice. The expanding gas accelerates aerosol droplets containing the molecules to be introduced into a cell or tissue. Aerosol droplets produced are typically less than 0.1 micron in diameter at the point of impact with the target cells. DNA carried in aerosol droplets of this small size penetrates cells only because of the speeds attained by the aerosol droplets. Speeds achieved by the aerosol beam method of the invention are supersonic and can reach 2000 meters/second. In a preferred embodiment, the process includes (I) culturing a source of cells, (II) optionally, pretreating cells to yield tissue with increased capacity for uptake and integration by aerosol beam technology, (III) transforming said tissue with an exogenous nucleotide sequence by the aerosol beam method of the invention, (IV) optionally, identifying or selecting for transformed tissue, (V) optionally, regenerating transgenic plants from the transformed cells or tissue, and (VI) optionally, producing progeny of said transgenic plants. This process is described in detail at Held et al., U.S. Pat. Nos. 6,809,232; 7,067,716; and 7,026,286 (all incorporated herein by reference in their entirety).

In accordance with the present invention, a transgenic plant can be produced that contains an introduced non-pollen preferred promoter. It can be combined with any one of the components set forth above.

In a further embodiment, plant breeding can be used to introduce the nucleotide sequences into other plants once transformation has occurred. This can be accomplished by any means known in the art for breeding plants such as, for example, cross pollination of the transgenic plants that are described above with other plants, and selection for plants from subsequent generations which contain the nucleic acid and/or express the amino acid sequence or trait. The plant breeding methods used herein are well known to one skilled in the art. For a discussion of plant breeding techniques, see Poehlman, J. M. and Sleper, D. A. (1995) *Breeding Field Crops,* 4th Edition, Iowa State University Press. Many crop plants useful in this method are bred through techniques that take advantage of the plant's method of pollination. A plant is self-pollinating if pollen from one flower is transferred to the same or another flower of the same plant. A plant is cross-pollinating if the pollen comes from a flower on a different plant. For example, in *Brassica,* the plant is normally self-sterile and can only be cross-pollinated unless, through discovery of a mutant or through genetic intervention, self-compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (*Zea mays* L.) can be bred by both self-pollination and cross-pollination techniques. Maize has male flowers, located on the tassel, and female flowers, located on the ear, on the same plant. It can self or cross-pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods to make one plant pool male sterile, and the other the male fertile pollen donor. This can be accomplished by hand detassling, cytoplasmic male sterility, or control of male sterility through a variety of methods well known to the skilled breeder. Examples of more sophisticated male sterility systems include those described by Brar et al., U.S. Pat. Nos. 4,654,465 and 4,727,219 and Albertsen et al., U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as Poehlman et al. (1995) supra.

Further, the plant, seed or tissue can be further processed into a plant product, such as including grain products such as flour, meal, and grits, or separated starches, oil, protein and oil and the like.

EXAMPLES

The following is presented as illustrative of an embodiment of the invention and does not limit the scope of the invention as otherwise set forth.

Example 1

Soybean Promoters Lacking Expression in Pollen

A screening was undertaken to identify promoters that lack expression in soybean pollen using gene-chip analysis. To achieve this goal, total RNA from leaf, root, and pollen tissues was isolated using 'Plant RNeasy Kit' of Qiagen. Duplicate preparations were made from each of these tissues on 2 different days. Over 30 μg of highly pure RNA samples from each tissue type were obtained from each replicate preparation. These samples were submitted to the Iowa State University Gene-Chip facility for analysis. Analysis of soybean gene expression for each tissue type was done in duplicate. A total of about 38,000 gene data points were collected per chip. From the results four gene candidates were chosen expressed at low or no levels in pollen but were expressed in the leaves and roots. These candidates were called GSO, GNR, 185, and 17. The complete sequences of these genes including their promoter and terminator sequences were obtained from the recently published soybean genome database (phytozome.net/search.php?show=blast&blastdb=soybean, University of California Regents, Center for Integrative Genetics, 2010). This information was used in designing the following specific primers to amplify the promoter regions:

```
GNR:
                                          (SEQ ID NO: 6)
GATCTTCATTTATCCATTGGGGTACTTGTTTC (SEQ ID NO: 7)
TGAGGAAATTAAATGAAAGGAAAAGAAAATTAGAG

GSO:
                                          (SEQ ID NO: 8)
GAAGGAGATCTAGTTCACTGGTTAAATAAGATGTG (SEQ ID NO: 9)
GGTCTACTGAGGCGTGTGGCTGGAGTGAGG

GNRter:
                                          (SEQ ID NO: 10)
TTAACCAGTGCATGATGCTGAATTAAATG (SEQ ID NO: 11)
TTATAATGTAGTTTCAACTTGAATCC 17:
                                          (SEQ ID NO: 12)
ATCCCATGGTCGCGGACGATGTAATAGAAC (SEQ ID NO: 13)
ATCGGATCCACCCGCCCATACATCGTAACCAC 185:
                                          (SEQ ID NO: 14)
ACTGCGGCCGCGAGTATGACCCTTGATGCCGC (SEQ ID NO: 15)
ACTGGATCCACCTTAGTTAGGATTTTGTGTTTT
```

Using the soybean Jack [See, Nickell, C. D., G. R. Noel, D. J. Thomas, and R. Waller (1990) Registration of 'Jack' soybean. *Crop Sci* 1365. 30] genomic DNA as a template and the specific primers, promoters were amplified by PCR. The amplicons were cloned in pGEM-T Easy vector and correct clones containing the GNR, GSO, 17, and 185 inserts were identified by restriction digestion analyses. The nucleotide sequences of the cloned GNR (FIG. 1), GSO (FIG. 2), 17 (FIG. 3) and 185 (FIG. 4) promoters were determined. Comparison (GAP) of these sequences to the GNR, GSO, 17, and 185 sequences reported in the 'soybean genome database' revealed that the cloned promoter sequences were >99.5% identical to the reported sequences.

The amplified GNR and GSO promoters cloned in pGEM-TEasy vectors were excised as EcoRI/BamHI fragments (1065 bp GNR fragment and 890 bp GSO fragment). These fragments were introduced into an EcoRI/BamHI digested plasmid vector. Subsequently, the GNR terminator (FIG. 5) was introduced into to these constructs (as AscI/SacI fragments) to generate pGNRproGNRter and pGSOproGNRter constructs.

Figure 7:
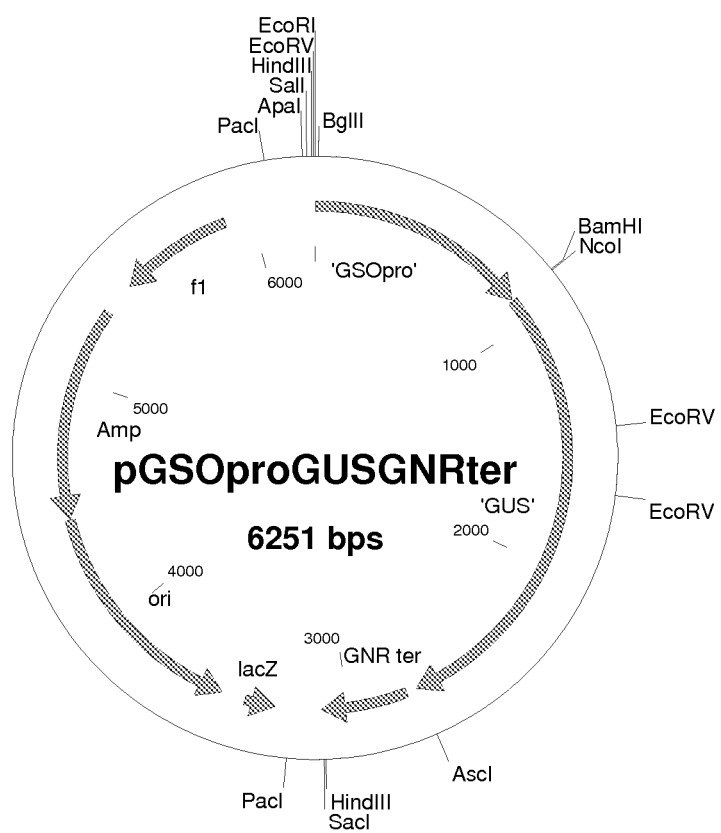
FIG. 7 shows a diagram of the pGSOproGUSGNRter construct.
Figure 8:
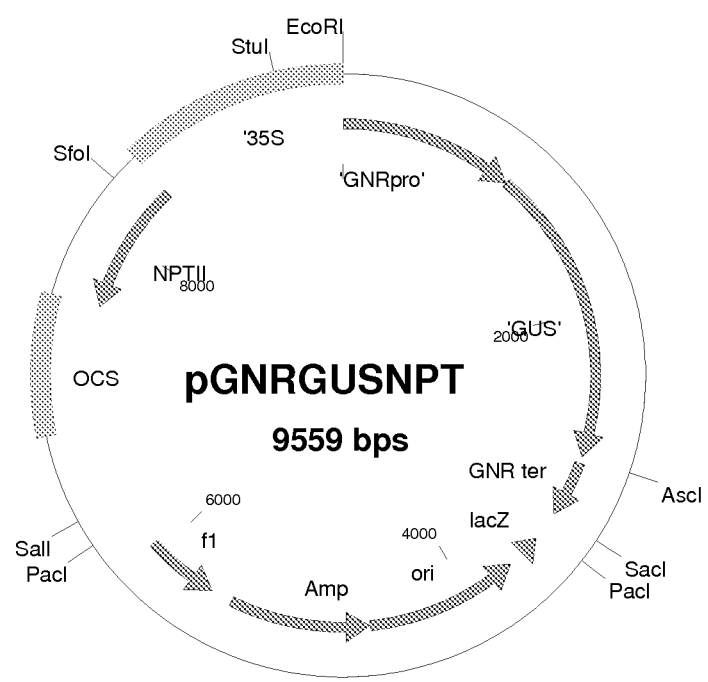
FIG. 8 shows a diagram of the pGNRGUSNPT construct.
Figure 9:
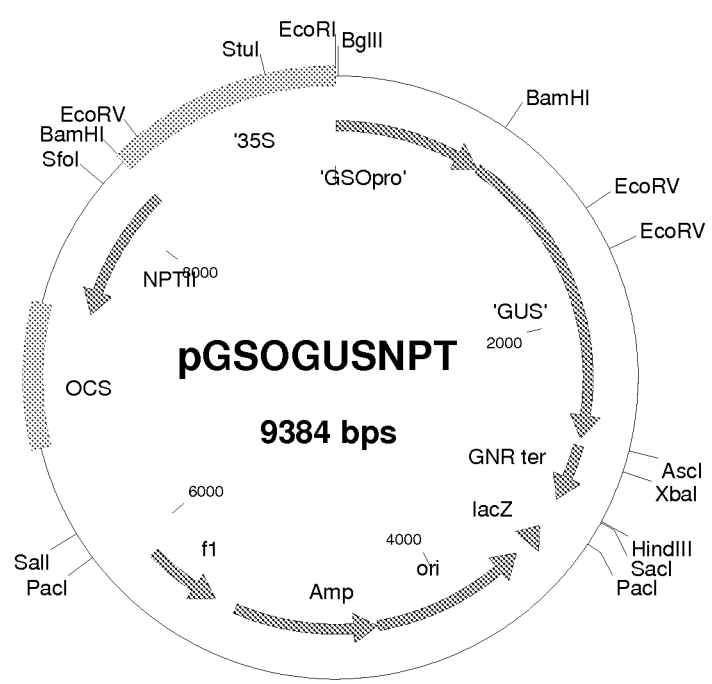
FIG. 9 shows a diagram of the pGSOGUSNPT construct.

A GUS gene was amplified as a BamHI/AscI fragment through PCR and the amplicon was cloned into pGEM-T vector. A correct pGEM-T/GUS clone was identified by restriction digestion analysis. The GUS insert from this clone was excised as a BamHI/AscI fragment and was introduced into BamHI/AscI-digested pGNRproGNRter and pGSOproGNRter backbones to generate pGNRproGUSGNRter and pGSOproGUSGNRter constructs, respectively (FIGS. 6 & 7). The pGNRproGUSGNRter and pGSOproGUSGNRter constructs were linearized with EcoRI and SalI. The NPTII cassette (35S NPTII Ocs) was removed as an EcoRI and SalI fragment and introduced into the EcoRI/SalI-digested pGNRproGUSGNRter and pGSOproGUSGNRter constructs to generate pGNRGUSNPT and pGSOGUSNPT, respectively (FIGS. 8 & 9). These constructs were used in the transformation of soybean.

Promoters 17 and 185 were amplified with PCR as is common in the art to facilitate cloning them upstream of a GUS gene. Primers used to amplify promoter 17 were (actcaattgacccgcccatacatcgtaaccactata) (SEQ ID NO: 16) and (atcggatcccgcggacgatgtaatagaactagctag) (SEQ ID NO: 17). Primers used to amplify promoter 185 were (actcaattggagtatgaccctgatgccgccaag) (SEQ ID NO: 18) and (actggatccaccttagttaggattttgtgttttgagtg) (SEQ ID NO: 19). The amplified bands were cloned into pGEM-T Easy vector according to the manufacturer Promega. The 17 and 185 promoters in pGEM-T were digested with MfeI and BamHI and cloned into the EcoRI and BamHI sites of pGSOproGUSGNRterNPT, thus, replacing the GSO promoter with the 17 and 185 promoters, respectively. The resulting constructs were called 17GUSNPT (FIG. 10) and 185GUSNPT (FIG. 11). These constructs were used in the transformation of soybean. Soybean was transformed according to the procedure described in U.S. Pat. No. 6,809,232, incorporated herein by reference in its entirety.

Transgenic plant tissue was evaluated for GUS expression using a histochemical staining procedure. Leaf tissue and pollen were incubated in the presence of the substrate X-gluc (Gold Biotechnology, Inc.) at a concentration of 0.5 mg/ml in 0.1 M sodium phosphate buffer pH 7.0 and 0.1% Triton-x-100 at 37.degree. C for 1-8 hours. Plants were obtained which expressed GUS in the leaves but no detectable expression in the pollen for the 17, 185, GNR and GSO promoters.

What is claimed is:

1. A method of expressing a heterologous nucleic acid molecule in a plant, the method comprising,
   (A) introducing into said plant a heterologous nucleic acid molecule operably linked to a promoter comprising a polynucleotide selected from the group consisting of:
   (a) a nucleotide sequence comprising SEQ ID NO: 1;
   (b) a nucleotide sequence comprising SEQ ID NO: 2;
   (c) a nucleotide sequence comprising SEQ ID NO: 3;
   (d) a nucleotide sequence comprising SEQ ID NO: 4; and
   (e) a functional fragment of any of sequences in parts (a)-(d), wherein said nucleotide sequence or said fragment directs expression of an operably linked heterologous nucleic acid molecule such that said nucleic acid molecule is expressed in leaf and is not expressed in pollen; and
   (B) detecting expression of said heterologous nucleic acid molecule in said plant tissue such that no detectable expression is found in pollen and said nucleic acid molecule expresses in leaf tissue.

2. The method of claim 1, wherein said heterologous nucleic acid molecule is expressed at lower levels in pollen cells of said plant than in other cells of said plant encodes a measurable product.

3. The method of claim 1, wherein said heterologous nucleic acid molecule encodes a polypeptide that confers tolerance to a herbicide.

4. The method of claim 1, wherein said heterologous nucleic acid molecule encodes a *Bacillus thuringiensis* polypeptide.

5. The method of claim 1, further comprising producing a grain product from said plant.

6. The method of claim 1 wherein said heterologous nucleic acid molecule is operably linked to SEQ ID NO:5.

7. The method of claim 1, further comprising introducing said promoter operably linked to said heterologous nucleic acid molecule into at least one plant, and selecting a plant in which said heterologous nucleic acid molecule is expressed in leaf tissue and in which said heterologous nucleic acid molecule has no detectable expression in pollen.

8. The method of claim 1, wherein said plant is crossed with a second plant.

9. The method of claim 1, wherein a progeny is produced from said plant.

10. The method of claim 2, wherein said measurable product is a polypeptide and the presence of said polypeptide is detected.

11. The method of claim 2, wherein said measurable product may be visually observed.

12. The method of claim 1, wherein said promoter is selected from the group consisting of:
   (a) a nucleotide sequence comprising SEQ ID NO: 1;
   (b) a nucleotide sequence comprising SEQ ID NO: 2;
   (c) a nucleotide sequence comprising SEQ ID NO: 3; and
   (d) a nucleotide sequence comprising SEQ ID NO: 4.

* * * * *

UNITED STATES PATENT AND TRADEMARK OFFICE
CERTIFICATE OF CORRECTION

PATENT NO.        : 8,648,230 B2                                        Page 1 of 1
APPLICATION NO.   : 13/051358
DATED             : February 11, 2014
INVENTOR(S)       : Bruce Held et al.

Figure 10:
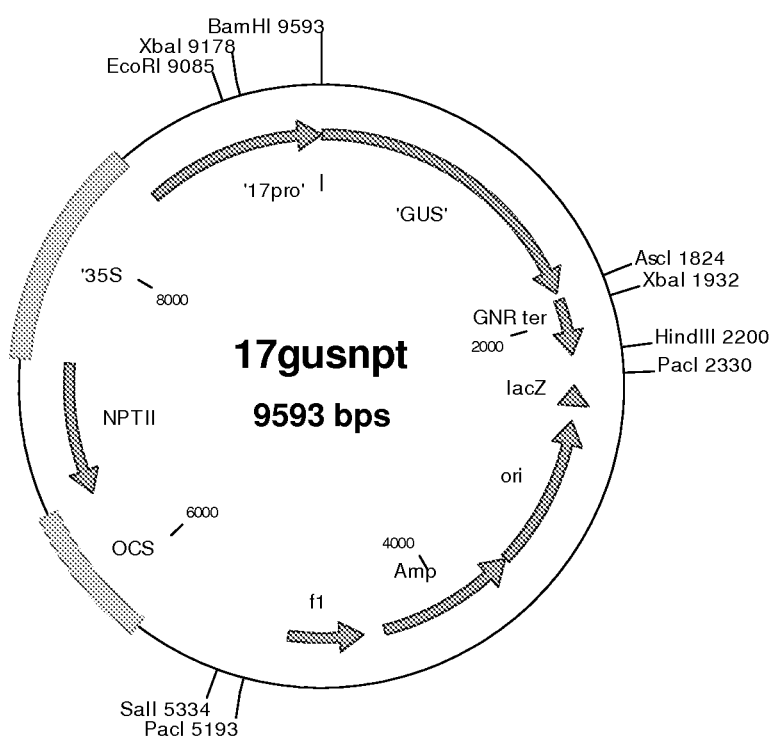
FIG. 10 shows a diagram of the 17GUSNPT construct.
Figure 11:
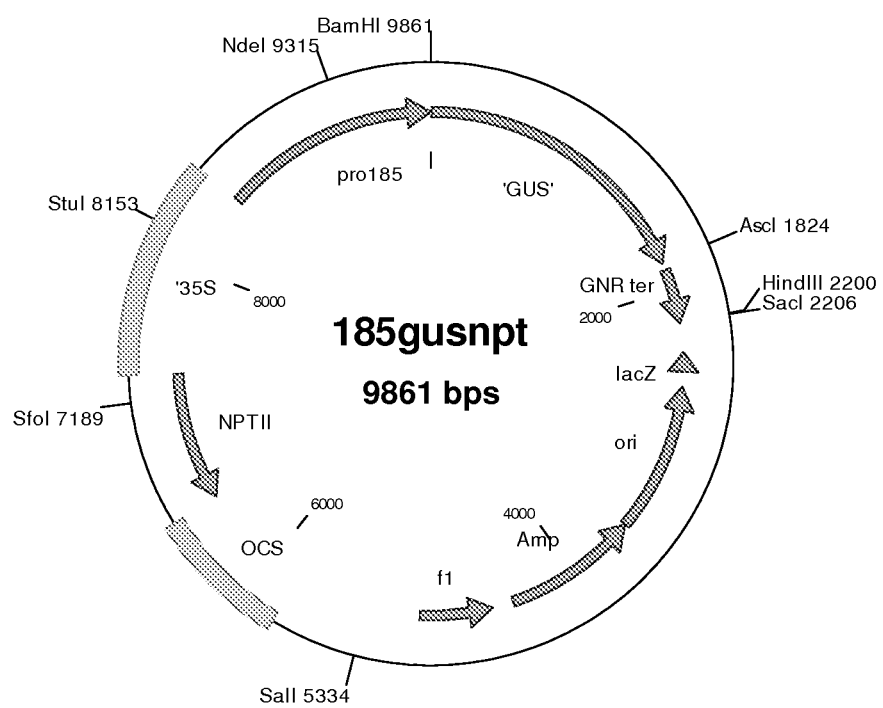
FIG. 11 shows a diagram of the 185GUSNPT construct.

It is certified that error appears in the above-identified patent and that said Letters Patent is hereby corrected as shown below:

In the Drawings
In Figure 5 after "sequence of" please delete "GNR" and insert therefore --SEQ ID NO 5--
In Figure 6 at where "GNRter" appears and "GNR ter" appears, please delete "GNRter" and "GNR ter" and insert therefore --ter--
In Figure 7 at where "GNRter" appears and "GNR ter" appears, please delete "GNRter" and "GNR ter" and insert therefore --ter--
In Figure 8 please delete "GNR ter" and insert therefore --ter--
In Figure 9 please delete "GNR ter" and insert therefore --ter--
In Figure 10 please delete "GNR ter" and insert therefore --ter--
In Figure 11 please delete "GNR ter" and insert therefore --ter--

In the Specification
At column 2, line 20 please delete "GNR" and insert therefore --SEQ ID NO 5--
At column 2, line 22 please delete "GNFT"ter" and insert therefore --SEQ ID NO 5ter--
At column 2, line 24 please delete "GNRter" and insert therefore --SEQ ID NO 5ter--
At column 28, line 45 please delete "GNR" and insert therefore --SEQ ID NO 5--
At column 29, line 12 please delete "GNR" and after terminator insert --of SEQ ID NO 5--
At column 29, line 14 at both instances where "GNter" appears please delete "GNRter" and insert therefore --SEQ ID NO 5ter--
At column 29, line 22 please delete "GNRter" and insert therefore --SEQ ID NO 5ter--
At column 29, line 23 at both instances where "GNRter" appears please delete "GNRter" and insert therefore --SEQ ID NO: 5ter--
At column 29, line 24 please delete "GNRter" and insert therefore --SEQ ID NO 5ter--
At column 29, line 25 at both instances where "GNRter" appears please delete "GNRter" and insert therefore --SEQ ID NO 5ter--
At column 29, line 29 at both instances where "GNRter" appears please delete "GNRter" and insert therefore --SEQ ID NO 5ter--
At column 30, line 14-15 please delete "GNRter" and insert therefore --SEQ ID NO 5ter--

Signed and Sealed this
Twenty-fifth Day of November, 2014

Michelle K. Lee
*Deputy Director of the United States Patent and Trademark Office*

SEQUENCE LISTING

<160> NUMBER OF SEQ ID NOS: 19

<210> SEQ ID NO 1
<211> LENGTH: 1059
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gatcttcatt tatccattgg ggtacttgtt tctttatgtt ttatatattt ctgtcactct      60
ctctaatttt ctttacacgg atactttta cttttattg aaaaacatag gatatgtatg      120
aatacatcac ttgcacttta ctttcatgca tggatattgt tctaatttct taatagaatt      180
tatcacagac caacacccaa acttgcttag taacctaaac taatttaata aaataaaaaa      240
aaatccctat tacattgatt tttgtttgag gaataactat tttttctttt tacattgatt      300
ttattttatt agtattagtt aaacttggat tcaatttttc agttaaaaaa actgggattc      360
aattttcaat cttaaattaa atatccttaa tattaaagag tctaactcaa ttaatttaat      420
aatgtgtaag atattataag ttttttgatt aagttcaatt catacaataa aataaataag      480
ataatgacaa gagatgttga aatatgtaaa tctaacctaa tttaatgcaa ctcgtcattc      540
ataaaaaaaa ggattggatt gggttagaaa ttctaatgta acccaatcct gatataaatt      600
tgtgggttac gataggatgg caaacttata atgcaactat tttttttttat ttgttaaaaa      660 tgatattttt attttttaaaa tataaaattt ataaatataa taaataaata cataataagt      720
ttataaaatt taaaaatgat attttttattt ttaagaaaca aaatcgctaa attagttgag      780
aatgcaaaac ttttaaaata ctactccatt tactataatt tttggaaata taattggtct      840
```

```
gacatagcca tagtacacag tcttttctc gatacttggt ttggttacgt ctctttcccc      900
acgacgcctc tatataactc gcccaatccc tccatctttc actcgttcaa aaacaaaacc     960
attctacctt ctccaaaacc atccaactct catgttcgaa gaaaacatac acaatctctt    1020
caaactctaa ttttcttttc ctttcattta atttcctca                            1059
```

```
<210> SEQ ID NO 2
<211> LENGTH: 884
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gaaggagatc tagttcactg gttaaataag atgtgggggt atttttttttt tttatcaaat     60 gggtgtgtga gtgttgtaaa ttcataatat gtttaattga tacggataaa aataaaccat    120
tataataaaa aattattatt ttatatttta attttatttta taaactagcc actaattttt    180
tattaatgaa atggtatgca ttttcatta tttttagttt atttccataa ataaaataat     240
tttgtagtat ttttaaatat ttttcaattt ttacatattt attgttataa aattataata    300
aaatgcatat gcagagaaag actttatatt atcattcaat cacaaattat cattaattat    360
tttaagataa taattttaaa gattatcaaa attatcatta tgatcaatga ttctttaaaa    420
aaagttactc tataacttt ttctcaataa attaactgaa ataaaatat aaaaacacac     480 ggtatggtcc acaaaaatta gttaagaaat tagttttgaa gttctatttt gttataattt    540
ttaaatctga tgcggtagta taaattccac aaaaataagt taataagcac atttaagaaa    600
ttaagcattc atccgagata ctctaattgg ataatttaaa cttttgtgtg agccgtacaa    660
ttaatatatg atataattat gtaataatat atagatacta atcgataaag atgtaataat    720
aacgtagaat ttgtactgat ggggctgtgc tggtcgtacc tgcacaactt agtgtactac    780
aacattggaa ttgtactaac acactttctt gtttatattg ccctgtaagg aatgggtaga    840
cctttgtcca aaatcctcac tccagccaca cgcctcagta gacc                     884
```

```
<210> SEQ ID NO 3
<211> LENGTH: 1110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atcggatcca cccgcccata catcgtaacc actatacacc attcaagcaa tacatgcatt     60
acatttacac ccaatggtaa ttaccctgtg acctcgccct actaattaat actacactcc    120
attcaacatt tttgccactg agcattacaa gatatagcat tttcaagaca atgtgcaata    180
ttaatgcata ctactctccc cgagtacact ccaagtcggt gaggaagtat gaactccaat    240
ccgtgttctg gagatgaatt tgagtaggtg ctggggttct gcgatacatc gtgaaaaatt    300
cagttaatcg ccgtcttgtc aggaaatgca tgcaaaacat tcatctgcca atacaaagaa    360
accctagtaa gacctcataa gctacagtac agtaaacagt atatgacaga caggatgttg    420
attacatatg cgtctcgttt tcaagggaca ctccaactct gcgcaagtag taatcacgca    480
cagagagaga gagagcaagc aaacagaaaa aaataaaaag aaaatgaaag gagacttctt    540
ctcatgattg ctacgtgacg ttagtagtgg gaatagagaa aaggaatcga gagaattcta    600
```

-continued

```
cttttttatt ttttaagaaa taagcataaa ataattcaat aactataata tcttaaaaca        660
aaagagacaa atggattttt ttttgtctag aaaaaaagag acttagcttt acacattata        720
ttaatattat atgataacat tatcatatct tattagcata ataaataaca aattacaaaa        780
taatagagta gttatccttt cttctcctag ttactttagg agaccttgtt aattagctat        840
gtagtgaaag tataacagag ttcaattatc atttaatcac tccctcagaa aaaattgatc        900
atttaaccac agatattctt aatctagctt ttcatgcaac cctatccgtc tatattacat        960
ctcatacaat acaaccctgc ccgtctatat aaggtccacg taccttgaac gttttctgca       1020
ttctcactat tctcctcatc ttcctctttt tctcaaccaa aaggggttca attctagcta       1080
gttctattac atcgtccgcg accatgggat                                       1110
```

<210> SEQ ID NO 4
<211> LENGTH: 1382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
actgcggccg cgagtatgac ccttgatgcc gccaagaaaa atttgttctg aattttcttt         60
ttttaaaaag ttacctatgt atttttatg ggagactttt tgctcaaaga attattataa        120
acattaaaat ataagtattg acaattatat atttaataaa taaatttaag attattgatt        180
aaactaacat aatttcatac taattaattc atacgttcgg tgatgtgata gaaattaata        240
tatatatata tatatatata tagaggtata ttttagttaa atttctcaat aagtttataa        300
gaaaagaaaa gataaccaat gtttctttca tacattaaaa tctaaattat acacgtcaac        360 attttaaaa gttttttatt aaattatttt caaagtgatg tataaatgtt ttgattttg         420 gagaaaaaat ttacctttc aatttttttc ttataattac ttattactgg acacaatttt        480
cttttatccc tttctaaatg tcttttaggc tgaaatcagc aatctggctt ttagactgaa        540
aataatttcc ccgcatgttt tggagtcgtc ttccttttct atctttttac tcccatttgc        600
ttagagattg aaattttgca ctacagtgaa cagtaggaaa taattgcatt tcgggtgact        660
ttggcttcag cttcagcaat tcagtgattt cagtctaatc tgtctgttac aatcggtttg        720
accacgaagt tccaccgaaa ggtactaaaa taatgtagat tttcattaac atatctaaaa        780
tttcaactct gagctatgtg accaagccat ataaaataca aactagtcat atgatcttga        840
ccttcgtcct taggaagaaa aagaaattat aaagtcaata tatagataat tacatcgatc        900
taaaagtatt cagctatgtt aaatttctaa atgataagt tttattagaa aaaaagcatc        960
tattatattt ttatataata agtgcttaat gctttatttc ttaattaaaa cctatctctt       1020
ttagatgttt aaaatcaatc ctaaagtcca atttaatgtt aacattttac ataaatatttt      1080 gctgttacct gaaatcatta agcagtaatt tggatgctaa atctctggac tagtaatctt       1140
taccatttaa tagtggacca agtttaatt aaagtggtgg gataagggc aaacctacat        1200 tccctcactc ttataatttg atcccacacc ttcccatgct tattttatt tttgttttcc       1260 actaagctca cagtataaat agggactaaa ctaaatccga aatgcaccat cacagaagca       1320
attaacatat tctcctctca ttctcactca aaacacaaaa tcctaactaa ggtggatcca       1380
gt                                                                     1382
```

<210> SEQ ID NO 5
<211> LENGTH: 368

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
ttaaccagtg catgatgctg aattaaatgc agaataagtg atttatcctg atagtgatga      60
tgaattggat ggcgtcatga ggaatagtgg attattttta tctagaaagt gtacgatggc     120
acatcttttg tactttaaat aggtgttgtg gtatcaggct aaatcacttc agcctgcaga     180
ttatgttcta taattagaaa tcttagttat ggttctcttt gtgtgactgt gtgaacaata     240
aaattgctta tgcatgaaca ttcagcaaaa taatactatg ttgtagaacc ttttcacgta     300
acttgtacga gagcgtatct tttttccat gagcatcact taggattcaa gttgaaacta      360
cattataa                                                              368
```

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
gatcttcatt tatccattgg ggtacttgtt tc                                    32
```

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
tgaggaaatt aaatgaaagg aaaagaaaat tagag                                 35
```

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
gaaggagatc tagttcactg gttaaataag atgtg                                 35
```

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
ggtctactga ggcgtgtggc tggagtgagg                                       30
```

<210> SEQ ID NO 10
<211> LENGTH: 29
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 10
ttaaccagtg catgatgctg aattaaatg                                           29

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttataatgta gtttcaactt gaatcc                                              26

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atcccatggt cgcggacgat gtaatagaac                                          30

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atcggatcca cccgcccata catcgtaacc ac                                       32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
actgcggccg cgagtatgac ccttgatgcc gc                                       32

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
actggatcca ccttagttag gattttgtgt ttt                                      33

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 16
actcaattga cccgcccata catcgtaacc actata                              36

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atcggatccc gcggacgatg taatagaact agctag                              36

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
actcaattgg agtatgaccc ttgatgccgc caag                                34

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
actggatcca ccttagttag gattttgtgt tttgagtg                            38
```